US009763874B2

(12) United States Patent
Pisani et al.

(10) Patent No.: US 9,763,874 B2
(45) Date of Patent: Sep. 19, 2017

(54) NANOPARTICLES LOADED WITH CHEMOTHERAPEUTIC ANTITUMORAL DRUG

(75) Inventors: Emilia Pisani, Fontenay Sous Bois (FR); Sophie Lebel-Binay, Villejuif (FR); Valérie Polard, Plabennec (FR)

(73) Assignee: Onxeo S.A. (FR)

( * ) Notice: Subject to any disclaimer, the term of this patent is extended or adjusted under 35 U.S.C. 154(b) by 0 days.

(21) Appl. No.: 14/009,021

(22) PCT Filed: Mar. 30, 2012

(86) PCT No.: PCT/EP2012/055756
§ 371 (c)(1),
(2), (4) Date: Sep. 30, 2013

(87) PCT Pub. No.: WO2012/131018
PCT Pub. Date: Oct. 4, 2012

(65) Prior Publication Data
US 2014/0024610 A1    Jan. 23, 2014

(30) Foreign Application Priority Data

Mar. 31, 2011 (EP) .................................. 11305364

(51) Int. Cl.
A61K 31/704 (2006.01)
A61K 9/19 (2006.01)
B82Y 5/00 (2011.01)
A61K 9/00 (2006.01)
A61K 9/51 (2006.01)
A61K 47/48 (2006.01)

(52) U.S. Cl.
CPC .......... *A61K 9/0019* (2013.01); *A61K 9/5138* (2013.01); *A61K 9/5161* (2013.01); *A61K 31/704* (2013.01); *A61K 47/48969* (2013.01); *B82Y 5/00* (2013.01); *A61K 9/19* (2013.01)

(58) Field of Classification Search
CPC ............ A61K 31/704; A61K 47/48969; A61K 9/0019; A61K 9/19; A61K 9/5138; A61K 9/5161; B82Y 5/00
See application file for complete search history.

(56) References Cited

U.S. PATENT DOCUMENTS

| 6,881,421 | B1 | 4/2005 | Silveira et al. | |
|---|---|---|---|---|
| 2004/0170613 | A1* | 9/2004 | Ferrara et al. | 424/93.21 |
| 2004/0202665 | A1* | 10/2004 | Lazarovits et al. | 424/178.1 |
| 2009/0061009 | A1 | 3/2009 | Schwarz et al. | |
| 2010/0234314 | A1* | 9/2010 | Berlinski | A61K 31/704 |
| | | | | 514/34 |

FOREIGN PATENT DOCUMENTS

EP        2 508 207 B1      5/2013
WO    WO-2009/108932 A2    9/2009

OTHER PUBLICATIONS

Duchene et al. (Abstract of: Ann Pharm Fr. 2001, 59(6):384-91).*
Bennis et al. (Abstract of: Eur. J. Cancer 1994;30A:89-93).*
el-Samaligy et al. (Abstract of: J Pharm Pharmacol 1986, 38(3):216-8).*
Sileni et al. (Cancer Chemother Pharmacol 1992, 30:221-225).*
Sparano et al. (Journal of Clinical Oncology 2001, 19(12):3117-3125).*
Poyanli et al. (Abstract of: Acta Radiol. 2001, 42(6):602-7) 2 pages.*
Wu et al. (The American Journal of the Medical Sciences 2009, 338:357-360).*
Hurst et al. (Interventional Neuroradiology 2007, CRC Press, p. 299).*
Sewa et al. (Annals of Internal medicine, 1982;96(2):133-139).*
Robert (Cancer Drug Delivery 1987,4(3):191-1999).*
Shapira et al. (Abstract of: Cancer. 1990, 65(4):870-3) 2 pages.*
Gabizon (Cancer Investigation 2001;19(4):424-436).*
Physicians Desk Reference 2003 pp. 2419-2423 (6 pages).*
Remington's Pharmaceutical Sciences 17th Edition, 1985:1149.*
Sacco et al. (Plos ONE 2010;5(1):e8933; 6 pages).*
Katten et al. (Investigational New Drugs 1992;10:191-199).*
The FDA's Drug Review Process; [online]; retrieved from: http://www.fda.gov/drugs/resourcesforyou/consumers/ucm143534.htm on Oct. 20, 2015; 4 pages.*
Chatterjee et al. (Cardiology 2010;115:155-162).*
Figueroa et al. (Respiratory Care. 2006;51(4):403-412).*
Eksborg et al. (Eur J Clin Pharmacol 1985;28:205-212).*
Couvreur et al., 1988, "Polyalkylcyanoacrylates as Colloidal Drug Carriers," Critical Reviews in Therapeutic Drug Carrier Systems 5(1)1-20.
Duchene et al., 1999, "Cyclodextrins in Targeting Application to Nanoparticles," *Advanced Drug Delivery Reviews* 36:29-40.
European Search Report from 11 305 364.9 dated Sep. 27, 2011.
International Preliminary Report on Patentability from PCT/EP2012/055756 dated Apr. 4, 2013.
PCT International Search Rep ort from PCT/EP2012/055756 dated May 29, 2012.

* cited by examiner

*Primary Examiner* — Ernst V Arnold
(74) *Attorney, Agent, or Firm* — Dechert LLP

(57) ABSTRACT

The invention relates to new therapeutic approaches for treating cancer, in particular hepatocellular carcinoma, with Nanoparticules loaded with a chemotherapeutic antitumoral agent. In particular, it relates to the treatment of cancer by administration of said Nanoparticules by intravenous infusion for at least 2 hours in order to prevent toxicological side effects and increase the benefit/risk ratio of the treatment.

20 Claims, No Drawings

NANOPARTICLES LOADED WITH CHEMOTHERAPEUTIC ANTITUMORAL DRUG

CROSS-REFERENCE TO RELATED APPLICATIONS

This application is a national stage entry of International Application No. PCT/EP2012/055756, filed Mar. 30, 2012, which claims priority under 35 U.S.C. §§119(a) and 365(b) to European Patent Application No. EP 11305364.9, filed Mar. 31, 2011.

FIELD OF THE INVENTION

The invention relates to the field of medicine, and in particular of oncology. It relates to a treatment of cancer, in particular hepatocellular carcinoma, with Nanoparticules loaded with at least one chemotherapeutic antitumoral drug.

BACKGROUND OF THE INVENTION

Cancer is characterized by uncontrolled growth of cells coupled with malignant behavior: invasion and metastasis. It is a major cause of mortality in most industrialized countries. Different ways of cancer treatment can be used: chemotherapy, radiotherapy, surgery, immunotherapy and hormonotherapy.

Chemotherapy can be defined as the use of chemotherapeutic antitumoral agents to treat cancer. Broadly, most chemotherapeutic antitumoral agents work by impairing mitosis (cell division) or DNA synthesis, effectively targeting fast-dividing cells.

Chemotherapeutic antitumoral agents are delivered most often parenterally, noteworthy intravenously (IV) or intra-arterially (IA). IV or IA chemotherapy can be given over different amounts of time, depending on the drug and the type of cancer to be treated.

Hepatocellular carcinoma (HCC) is the fifth most common cancer in men (523,000 cases worldwide) and the seventh in women (226,000 cases worldwide), and most of the burden is in developing countries, where almost 85% of the cases occur, and particularly in men: the overall male/female ratio is about 4/1. The regions of high incidence are Eastern and South-Eastern Asia, Middle and Western Africa, but also Melanesia and Micronesia/Polynesia. Low rates are estimated in developed regions, with the exception of Southern Europe where the incidence in men (ASR 10.5 per 100,000) is significantly higher than in other developed regions (Globocan 2008, WHO, International Agency for Research on Cancer—IARC—, Cancer Incidence and Mortality Worldwide 2008).

There were an estimated 694,000 deaths from liver cancer in 2008 (477,000 in men, 217,000 in women), and because of its high fatality (overall ratio of mortality to incidence of 0.93), liver cancer is the third most common cause of death from cancer worldwide. The geographical distribution of the mortality rates is similar to that observed for incidence (Globocan 2008, WHO, International Agency for Research on Cancer—IARC—, Cancer Incidence and Mortality Worldwide 2008).

HCC usually occurs in people suffering from cirrhosis or chronic liver disease (CLD). All factors favoring the development of CLD or cirrhosis are consequently risk factors for HCC. The main etiologic factors are hepatitis B virus infection (HBV; 53%), hepatitis C virus infection (HCV; 25%), alcoholic liver diseases (ALD; 15-43%) or dysmetabolic disorders such as Non Alcoholic Steato-Hepatitis (NASH; 20%) obesity and diabetes. Other factors are less frequent: haemochromatosis, other chronic biliary or inflammatory liver diseases. Aflatoxins, produced by the fungi *Aspergillus flavus* and *Aspergillus parasiticus* grown on grains, peanuts, and other food products, are hepatotoxic agents and chronic exposure to these mycotoxins leads to development of HCC. The effects of chemicals are still debated and not prominent.

Current therapeutic strategies for HCC can be divided into curative treatments such as surgical interventions (tumor resection and liver transplantation), percutaneous interventions (ethanol injection, radiofrequency thermal ablation), or palliative treatments such as transarterial interventions (mainly transarterial chemoembolization or TACE), systemic therapies and experimental strategies (H. C. Spangenberg, R. Thimine, H. E. Blum, Biologics:Targets & Therapy, 2008, 2(3), 453). In carefully selected patients, resection and liver transplantation, allow a 5-years survival from 60% to 70%. Unfortunately, most patients in Western countries present an intermediate or advanced HCC at diagnosis, with the consequent inability to use these curative treatments (L. Faloppi, M. Scartozzi, E. Maccaroni, P. M. Di Pietro, R. Berardi, M. Del Prete, S. Cascinu, Cancer Treat. Rev., 2011, 37(3), 169).

Among palliative treatments, intra-arterial approach with chemoembolization (TACE) has shown to induce objective responses in 16-55% of patients, although many randomized trials did not show any survival benefit. Unfortunately, TACE is known to be often accompanied by severe side effects like hepatic failure or renal dysfunction (K. Kamada, T. Nakanishi, M. Kitamoto, H. Aikata, Y. Kawakami, K. Ito, T. Asahara, G. Kajiyama, J. Vasc. Interv. Radiol., 2001, 12(7), 847).

Until recently, for patients with advanced HCCs no therapy was available that prolonged overall survival (OS), indicating the need for new targeted-therapies (H. C. Spangenberg, R. Thimine, H. E. Blum, Biologics:Targets & Therapy, 2008, 2(3), 453). In 2007 and for the first time, sorafenib (Nexavar®), a multikinase inhibitor, showed an increase even modest, of the overall survival over placebo in patients with unresectable HCC. Beside this agent, various different molecules are currently tested in advanced stage HCC among which Brivanib, another oral multikinase inhibitor being currently tested in several phase III studies (H. C. Spangenberg, R. Thimine, H. E. Blum, Biologics: Targets & Therapy, 2008, 2(3), 453—K. Almhanna, P A Philip, Onco. Targets Ther., 2009, 18(2), 261).

Even though sorafenib is the standard of care for advanced stage HCC and is registered for the treatment of HCC without restrictions by the European Medicines Agency (EMA) and the Food and Drug Administration (FDA), the narrow inclusion criteria of the clinical trials leave many patients without proven efficacious treatment with regard to their disease stage. Moreover, since treatment failure happens in some patients on sorafenib, there still remains a medical need for those patients to improve treatment efficacy, drug regimen and overall tolerance, and to overcome resistance (M. Peck-Radosavljevic, Therap. Adv. Gastroenterol. 2010, 3(4), 259).

HCC is known as hypervascular solid cancer characterized by a high degree of drug resistance (T. Wakamatsu, Y. Nakahashi, D. Hachimine, T. Seki, K. Okazaki, Int. J. Oncol., 2007, 31(6), 1465). The mechanisms of this chemoresistance in HCC are multiple. However, the more common mechanism is related to the multidrug resistance (MDR) transporters, P-gp and MRP pumps (D. M. Bradshaw, R. J. Arceci, J. Clin. Oncol., 1998, 16(11), 3674. Review. Erratum in: J. Clin. Oncol., 1999, 17(4), 1330). These pumps allow tumour cells to efflux different types of chemotherapeutic agents into the extracellular environment (Y. Chen, S. M. Simon, J. Cell Biol. 2000, 148(5), 863). Chemoresistance related to the MDR phenotype may be intrinsic or be acquired during chemotherapy. Chemoresistance, whether spontaneous or acquired is a serious concern in cancer treatment. HCC is often intrinsically chemoresistant which is the major cause for failure of its therapy (R. Perez-Tomas, Curr Med. Chem., 2006, 13(16), 1859, Review). This poses a great obstacle in chemotherapy for cancer because higher doses of drugs need to be administered and in turn may cause severe adverse effects (F. Yan, X. M. Wang, Z. C. Liu, C. Pan, S. B. Yuan, Q. M. Ma, Hepatobiliary Pancreat. Dis. Int. 2010, 9(3), 287). Chemoresistance affects major chemotherapeutic agents and especially anthracyclins (like doxorubicin), vinca-alkaloids, epipodophyllotoxins or taxanes. The poor efficacy of chemotherapeutic agents attributed to the overexpression of the MDR gene underlines the need to develop new treatment strategies for HCC, which could take into account the resistance issues.

Doxorubicin is a chemotherapeutic compound, efficacy of which has been shown in several cancers including HCC. However, IV infusion of doxorubicin in HCC is modest with objective response rate of 5-10%. A large, randomized, multicentre clinical trial compared the efficacy of doxorubicin 60 mg/m2 administered through the IV route and thymitaq a direct thymidilate synthase inhibitor (Porta C., 2006). In the 446 randomized patients with unresectable HCC, the effect of doxorubicin was found modest. The modest effect of doxorubicin in HCC patients is assumed to result from multidrug resistance (MDR) mechanisms related to overactivity of PgP and MRP cellular pumps. Many strategies have been evaluated to overcome the resistance issues, including the use of Pgp and MRP inhibitors. The development of these drugs has been stopped due to their safety profile.

In HCC, new therapeutic strategies using cytotoxic agents were developed by hepatic intra-arterial (IA) injection in order to reduce the systemic toxicity, to induce important hepatic tumour necrosis and to save the healthy hepatic parenchyma.

The technology described in patents EP1056477, and its US equivalent U.S. Pat. No. 6,881,421, use polyalkylcyanoacrylate (PACA) polymer to formulate active ingredients into Nanoparticules. EP1056477, and its US equivalent U.S. Pat. No. 6,881,421, indicate the use of a complexing agent to complex the active ingredient during preparation of the nanoparticle so as to protect the active ingredient against chemical reactions that are necessary for the formation of the particle. Therefore, the active ingredient is advantageously associated in a non-covalent manner with the particle and protected from reactions or degradation. Nanoparticules comprising a pharmaceutically active ingredient, a polymer such as poly(alkylcyanoacrylate) and a complexing agent such cyclodextrins, are thus taught in EP1056477, and in its US equivalent U.S. Pat. No. 6,881,421.

Doxorubicin loaded in said Nanoparticules (hereinafter referred to as "Nanoparticules loaded with Doxorubicin") is a drug formulation that associates a kind of PACA, poly-isohexylcyanoacrylate (PIHCA), Nanoparticules with the chemotherapeutic agent doxorubicin.

Said Nanoparticules displays original mechanisms to bypass MDR that can be summarized as follow:

Nanoparticules loaded with Doxorubicin adsorbs to the surface of tumour cells and releases the entrapped doxorubicin close to the cell membrane which leads to a high local gradient concentration (Colin de Verdière A, Cancer Chemother Pharmacol. 1994; 33(6):504-8).

The nanoparticles degrade and release soluble polycyanoacrylic acid which might interact with the plasma membrane and contribute to improve the intracellular delivering of doxorubicin (De Verdière A C, Br J. Cancer. 1997; 76(2):198-205).

The soluble polymer could also mask the positive charge of doxorubicin thus preventing its effluxing by the Pgp (De Verdière 1997, Br J. Cancer. 1997; 76(2):198-205), acting as an ion pair without any covalent linkage). The direct interaction with MDR pumps (Pgp and MRP) is thus avoided.

In man, the efficacy and safety of Nanoparticules loaded with Doxorubicin through the hepatic intra-arterial route have been evaluated in 2 clinical trials: in one open phase I-II and one randomized phase II clinical trial (Table 1).

TABLE 1

Summary of Study Designs for Clinical development of Nanoparticules loaded with Doxorubicin

| Phase/Study number | Description | Route Dosage | Population | Patients planned/complete | Status |
|---|---|---|---|---|---|
| Phase I/II BA/2002/03/02 | Open MC SD Esc dose | Hepatic IA 10 mg/m$^2$ 20 mg/m$^2$ 30 mg/m$^2$ 35 mg/m$^2$ 40 mg/m$^2$ | Advanced HCC | 21/20 | Completed |
| Phase II/III BA/2006/03/03 | Open, MC R PG | Hepatic IA 30 mg/m$^2$ every 4 weeks max 3 injections | Advanced HCC | 200/28 | Stopped |

The study BA2002/03/02 (phase VII study in patients with advanced HepatoCellular Carcinoma) was carried out according to a multicentre, open, dose-escalation design in patients suffering from HCC. Nanoparticules loaded with Doxorubicin was to be injected through hepatic intra-arterial (IA) route as a bolus. Successive cohorts of 3 patients were injected a single 10, 20 and 30 mg/m$^2$ dose of Nanoparticules loaded with Doxorubicin. As the 30 mg/m$^2$ dose was well tolerated, the protocol was amended to assess 40 mg/m$^2$ and then 35 mg/m$^2$. As these 2 doses were considered toxic, additional patients were given 30 mg/m$^2$ Nanoparticules loaded with Doxorubicin dose in 15 minutes. Two patients received a second IA dose of Nanoparticules loaded with Doxorubicin and one patient received 3 IA infusions.

Twenty patients were included in this study. Apart from the serious respiratory TEAEs (Treatment Emergent Adverse Events) reported at 35 and 40 mg/m$^2$, tolerance was acceptable; most of the TEAEs were short lasting and of mild severity. All were reversible without sequellae. Overall, 50% of the non-serious TEAEs were expected as already reported with free doxorubicin. The most frequent TEAE were leukopenia (n=13; 65%), neutropenia (n=12; 60%), nausea (n=10; 50%), anaemia and abdominal pain (n=9; 45%), asthenia, fever, alopecia (n=6; 30%) and cough (n=5; 25%). Increase in transaminases was reported in 11 patients (55%) and was expected as likely related to treatment efficacy. Two patients had serious Acute Respiratory Distress Syndrome (ARDS) at the Nanoparticules loaded with Doxorubicin dose of 35 mg/m2.

Efficacy data clearly demonstrated a signal of efficacy with a mean and median survival of 548 and 315 days respectively, an objective response rate of 65 to 80% according to clinical study criteria.

On the basis of these data, the efficacy and safety of an hepatic IA 15-minute infusion of Nanoparticules loaded with Doxorubicin was compared to those of standard of care treatment.

The second study BA2006/03/03 (Phase II/III study in patients with advanced HCC) was carried out according to a multicentre, comparative, open, randomized (with a 2/1 ratio) design in patients suffering from advanced HCC. Nanoparticules loaded with Doxorubicin was injected through IA route as a 15-minute infusion at the dose of 30 mg/m$^2$, preceded and followed by an oral premedication with methylprednisone. Fifty patients were to be included in the 1st part of the study. Three Nanoparticules loaded with Doxorubicin infusions were to be received by 33 patients at 4-week intervals and each of the other 17 patients were to receive the best standard of care treatment adapted to the severity of the disease. At the end of this 1st phase, if Nanoparticules loaded with Doxorubicin was considered active in ⅔ of patients (patients free of local progression at 3 months), then 150 additional patients were to be enrolled.

This study was prematurely discontinued when 28 patients had been enrolled because of the occurrence of ARDS leading to death in 2 patients treated with Nanoparticules loaded with Doxorubicin. 17 patients had received 39 Nanoparticules loaded with Doxorubicin infusions and 11 were randomized in the control group. No patients died of ARDS in the control group.

Despite many patients in the Nanoparticules loaded with Doxorubicin group did not complete treatment according to the protocol (3 infusions 4-week apart) because of the premature discontinuation of the trial, 63% of patients in the Nanoparticules loaded with Doxorubicin group were free of local progression at month 3 (versus 75% showing local progression in the control group). The patients enrolled were monitored and survival was recorded up to February 2011. Overall survival was significantly longer in the Nanoparticules loaded with Doxorubicin group than in the control group. At this time point, the mean and median overall survival was 952 days for Nanoparticules loaded with Doxorubicin group versus 449 days for control.

In addition, survival was significantly much longer in patients having completed 3 courses of Nanoparticules loaded with Doxorubicin as requested in the protocol. The mean and median overall survival was twice as long in the Nanoparticules loaded with Doxorubicin group having received 3 IA injections as in the control group. Likewise survival was much longer in patients having completed 3 courses of Nanoparticules loaded with Doxorubicin than in those having received only one or 2 IA injections of 30 mg/m2 Nanoparticules loaded with Doxorubicin. These data confirmed the strong signal of efficacy of Nanoparticules loaded with Doxorubicin in the treatment of patients suffering from advanced HCC.

Hence, albeit very promising in term of efficacy, use of Nanoparticules loaded with chemotherapeutic drug, such as Nanoparticules loaded with Doxorubicin, in cancer treatment, and in particular HCC treatment, is not currently possible because of its severe pulmonary adverse events. New approaches allowing safer use, reducing the probability of occurrence of pulmonary adverse events and their severity under acceptable limits owing to the benefit/risk ratio are then needed. In particular, it would be very advantageous to decrease the pulmonary adverse events induced by these Nanoparticules and at the same time to maintain the good efficacy already observed.

SUMMARY OF THE INVENTION

The inventors succeeded in obtaining a suitable animal model for the severe pulmonary adverse events and, then, have surprisingly found that severe toxicological side effects, in particular lung injuries, associated with intra-arterial or intravenous administration of Nanoparticules loaded with a chemotherapeutic agent, can be prevented by intravenous or intra-arterial infusion of said Nanoparticules for several hours.

On this basis, the present invention concerns Nanoparticules comprising at least one chemotherapeutic antitumoral agent, at least one poly(alkylcyanoacrylate) and at least one cyclodextrin, for use for treating a cancer, wherein the Nanoparticules are administered by intravenous or intra-arterial infusion for at least 2 hours. In particular, Nanoparticules can be administered by intravenous or intra-arterial infusion for between 2 and 24 hours, more particularly for between 4 and 12 hours, even more particularly for about 6 hours. In a particular embodiment, the administration is by intravenous infusion.

Preferably, the poly(alkylcyanoacrylate) polymer comprised in the Nanoparticules is a polyisohexylcyanoacrylate polymer.

The Nanoparticules used in the invention may comprise said at least one chemotherapeutic agent at a concentration from 0.01 to 200 mg/g of Nanoparticules, from 0.1 to 70% w/w of said at least one cyclodextrin and from 1 to 25% w/w of said at least one poly(alkylcyanoacrylate).

The chemotherapeutic antitumoral agent comprised in the Nanoparticules may be selected from the group consisting of anthracyclines, topoisomerase inhibitors, spindle poison plant alkaloids, alkylating agents, anti-metabolites, ellipticine and harmine, and any combination thereof. Preferably, the chemotherapeutic antitumoral agent is an anthracycline. More preferably, the chemotherapeutic agent is selected from the group consisting of doxorubicin, daunorubicin, epirubicin, idarubicin, valrubicin, pirarubicin, zorubicin, aclarubicin, detorubicin, caminomycin, morpholinodoxorubicin, morpholinodaunorubicin, methoxymorpholinyldoxorubicin, any pharmaceutically acceptable salt thereof, and any combination thereof. In a particularly preferred embodiment, the chemotherapeutic antitumoral agent is doxorubicin or any pharmaceutically acceptable salt thereof. In this embodiment, the dosage of doxorubicin may be from about 10 to about 75 mg/m$^2$, from about 10 to about 60 mg/m$^2$, from about 10 to about 45 mg/m$^2$, from about 10 to about 30 mg/m$^2$, from about 20 to about 30 mg/m$^2$. In a particular embodiment, the dosage of doxorubicin may be about 20 mg/m$^2$ or 30 mg/m$^2$.

The cancer treated with the Nanoparticules may be is a solid tumor or a hematopoietic tumor, preferably selected from the group consisting of hepatocellular carcinoma, acute lymphoblastic leukemia, acute myeloblastic leukemia, chronic myelogenous leukemia, Hodgkin's disease, diffuse large B-cell lymphoma, small cell lung cancer, colorectal cancer, pancreas cancer, breast cancer, ovary cancer, uterine cancer, cervix cancer, head and neck cancer, brain cancer, blade cancer, multiple myeloma, neuroblastoma, Edwing's sarcoma, osteosarcoma, soft tissue sarcoma, thyroid cancer, prostate cancer, stomach cancer, nephroblastoma, Kaposi's sarcoma, and non-Hodgkins lymphoma. In a particularly preferred embodiment, the cancer is a hepatocellular carcinoma.

In another aspect, the present invention concerns a method for treating cancer, wherein the method comprises administering by intravenous or intra-arterial infusion for at least 2 hours, a therapeutically effective amount of Nanoparticules comprising at least one chemotherapeutic agent, at least one poly(alkylcyanoacrylate) and at least one cyclodextrin to a patient in need of such treatment. Preferably, Nanoparticules are administered in the form of a pharmaceutical composition as described above. All embodiments disclosed above for the Nanoparticules are encompassed in this aspect. In a particular embodiment, the administration is by intravenous infusion.

In further aspect, the present invention concerns the use of Nanoparticules comprising at least one chemotherapeutic agent, at least one poly(alkylcyanoacrylate) and at least one cyclodextrin for the treatment of cancer, said Nanoparticules being administered by intravenous or intra-arterial infusion for at least 2 hours. All embodiments disclosed above for the Nanoparticules are encompassed in this aspect. In a particular embodiment, the administration is by intravenous infusion.

In a last aspect, the present invention concerns the use of Nanoparticules comprising at least one chemotherapeutic agent, at least one poly(alkylcyanoacrylate) and at least one cyclodextrin, for the manufacture of a pharmaceutical preparation for the treatment of cancer, said pharmaceutical composition being administered by intravenous or intra-arterial infusion for at least 2 hours. All embodiments disclosed above for the Nanoparticules are encompassed in this aspect. In a particular embodiment, the administration is by intravenous infusion.

DETAILED DESCRIPTION OF THE INVENTION

As preliminary work to the present invention, the inventors have established and assessed a rat model to investigate respiratory adverse events observed in previous clinical trials for treatment of hepatocellular carcinoma by hepatic intra-arterial infusion of doxorubicin formulated into Nanoparticules comprising a poly(alkylcyanoacrylate) polymer and a cyclodextrin (hereinafter referred to as "Nanoparticules loaded with Doxorubicin"). Using this model, they have herein demonstrated that intravenous infusion of said Nanoparticules for at least 2 hours allows to strongly reduce toxicological side effects, in particular lung injuries, compared to bolus intravenous injection at the same dose. This new therapeutic approach allows safer use of Nanoparticules and then dramatically increases the benefit/risk ratio.

Accordingly, in a first aspect, the present invention concerns Nanoparticules comprising at least one chemotherapeutic antitumoral agent for use for treating a cancer, wherein the Nanoparticules are to be administered by intravenous or intra-arterial infusion for at least 2 hours.

The one skilled in the art, considering the decrease of pulmonary toxicity induced by said nanoparticules thanks to their intravenous infusion for at least 2 hours would have expected a similar decrease with their intra-arterial infusion for at least 2 hours.

Indeed, an analytical model for intra-arterial versus intravenous infusion of doxorubicin is known in the state of the art, and shows that the two doxorubicin concentration decay curves are similar. Hence, the same theoretical curve is fitted and used for both cases ("An analytical model for intra-arterial versus intravenous infusion of Adriamycin", Logan S E et al., Biomed Sci Instrum. 1989; 25:239-46). This article indicates that even if these observations were made for bolus injections, similar relationships exist for continuous infusion. Indeed, the continuous infusion can be understood as a series of infinitesimal bolus injections, each one behaving as described in said analytical model.

Moreover, the state of the art confirms that in patients who received doxorubicin through a systemic vein, the drug level in the peripheral blood were comparable to those obtained from the peripheral blood of patient receiving doxorubicin intra-arterially. (comparison of Regional versus Systemic Chemotherapy with Adriamycin, Didolkar et al., Ann. Surg., March 1978, Vol. 187, No. 3, p. 332-336).

The Nanoparticules used in the present invention comprise at least one chemotherapeutic antitumoral agent, at least one poly(alkylcyanoacrylate) polymer, and at least one compound able to form a complex with the chemotherapeutic antitumoral agent, preferably chosen from among the cyclical oligosaccharides, in particular from among the cyclodextrins. Such Nanoparticules have been previously described in the European patent EP 1 056 477 and its U.S. equivalent U.S. Pat. No. 6,881,421, which are herein enclosed by reference.

The poly(alkylcyanoacrylate) polymer may be linear or branched, preferably branched. The alkyl group of the poly(alkylcyanoacrylate) may be linear or branched, preferably branched. In a particular embodiment, the poly(alkylcyanoacrylate) polymer is a poly($C_1$-$C_{12}$ alkylcyanoacrylate), preferably a poly($C_4$-$C_{10}$ alkylcyanoacrylate), more preferably a poly($C_6$-$C_8$ alkylcyanoacrylate). In a preferred embodiment, the poly(alkylcyanoacrylate) polymer is a polyisohexylcyanoacrylate. The monomer corresponding to the latter polymer is available, for instance under the trademark Monorex® by Bioalliance Pharma (France).

The cyclodextrin may be neutral or charged, native (cyclodextrins $\alpha, \beta, \gamma, \delta, \epsilon$), branched or polymerized, or even chemically modified, for example, by substitution of one or more hydroxypropyls by groups such as alkyls, aryls, arylalkyls, glycosidics, or by etherification, esterification with alcohols or aliphatic acids. Among the above groups, particular preference is given to those chosen from the group consisting of hydroxypropyl, methyl-m and sulfobutylether groups, and mixtures thereof. In a preferred embodiment, the cyclodextrin is selected from the group consisting of hydroxypropyl-beta-cyclodextrin and/or randomly methylated-beta cyclodextrin, and mixtures thereof.

As used herein, the term "chemotherapeutic agent" or "chemotherapeutic antitumoral agent" refers to any chemical compound or drug with anti-cancer activity that inhibits or halts the growth of cancerous cells or immature pre-cancerous cells, kills cancerous cells or immature pre-cancerous cells, increases the susceptibility of cancerous or pre-cancerous cells to other chemotherapeutic agents, and/or inhibits metastasis of cancerous cells.

In a particular embodiment, the chemotherapeutic agent is selected from the group consisting of anthracyclines, topoisomerase I and/or II inhibitors, spindle poison plant alkaloids, alkylating agents, anti-metabolites, ellipticine and harmine.

Anthracyclines (or anthracycline antibiotics) are derived from *Streptomyces* bacteria. These compounds are used to treat a wide range of cancers, including for example hepatocellular carcinoma, leukemias, lymphomas, and breast, uterine, ovarian, and lung cancers. Anthracyclines have three mechanisms of action: (i) inhibition of DNA and RNA synthesis by intercalating between base pairs of the DNA/

RNA strand, thus preventing the replication of rapidly-growing cancer cells; (ii) inhibition of topoisomerase II enzyme, preventing the relaxing of supercoiled DNA and thus blocking DNA transcription and replication; and (iii) creation of iron-mediated free oxygen radicals that damage the DNA and cell membranes. Anthracyclines include, but are not limited to doxorubicin (also named adriamycin), daunorubicin, epirubicin, idarubicin, valrubicin, pirarubicin, zorubicin, aclarubicin, detorubicin, caminomycin, morpholinodoxorubicin, morpholinodaunorubicin, methoxymorpholinyldoxorubicin, and their pharmaceutically acceptable salts thereof. Preferably, the anthracycline is selected from the group consisting of doxorubicin, daunorubicin, epirubicin, pirarubicin, zorubicin and aclarubicin, and any pharmaceutically acceptable salt thereof. In a preferred embodiment, the anthracycline is doxorubicin or any pharmaceutically acceptable salt thereof.

Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins derivatives Camptothecin derivatives refer to camptothecin analogs such as irinotecan, topotecan, hexatecan, silatecan, lutortecan, karenitecin (BNP1350), gimatecan (ST1481), belotecan (CKD602), or their pharmaceutically acceptable salts. Examples of type II topoisomerase inhibitors include, but are not limited to, amsacrine, etoposide, etoposide phosphate and teniposide They are semisynthetic derivatives of epipodophyllotoxins, alkaloids naturally occurring in the root of American Mayapple (*Podophyllum peltatum*). In a particular embodiment, the topoisomerase inhibitor is selected from the group consisting of irinotecan, its active metabolite SN38 and topotecan, and any pharmaceutically acceptable salt thereof. In a preferred embodiment, the topoisomerase inhibitor is irinotecan.

Spindle poison plant alkaloids are derived from plants and block cell division by preventing microtubule function, essential for cell division. These alkaloids include, but are not limited to, vinca alkaloids (like vinblastine, vincristine, vindesine, vinorelbine and vinpocetine) and taxanes. Taxanes include, but are not limited to, paclitaxel, docetaxel, larotaxel, cabazitaxel, ortataxel, tesetaxel, and their pharmaceutically acceptable salts. Preferably, the taxane is selected from the group consisting of paclitaxel and docetaxel, and any pharmaceutically acceptable salt thereof. Paclitaxel was originally derived from the Pacific yew tree. Docetaxel is a semi-synthetic analogue of paclitaxel. In contrast to the taxanes, the vinca alkaloids destroy mitotic spindles. Both taxanes and vinca alkaloids are therefore named spindle poisons or mitosis poisons, but they act in different ways.

Alkylating agents are so named because of their ability to add alkyl groups to many electronegative groups under conditions present in cells. They impair cell function by forming covalent bonds with the amino, carboxyl, sulfhydryl, and phosphate groups in biologically important molecules. Noteworthy, their cytotoxicity is thought to result from inhibition of DNA synthesis. Alkylating agents include, but are not limited to, mechlorethamine, cyclophosphamide, chlorambucil, ifosfamide and platinum compounds such as oxaliplatin, cisplatin or carboplatin.

An anti-metabolite is a chemical that inhibits the use of a metabolite, which is part of normal metabolism. Such substances are often similar in structure to the metabolite that they interfere with. The presence of anti-metabolites halters cell growth and cell division.

Purine or pyrimidine analogues prevent the incorporation of nucleotides into DNA, stopping DNA synthesis and thus cell divisions. They also affect RNA synthesis. Examples of purine analogues include azathioprine, mercaptopurine, thioguanine, fludarabine, pentostatin and cladribine. Examples of pyrimidine analogues include 5-fluorouracil (5FU), which inhibits thymidylate synthase, floxuridine (FUDR) and cytosine arabinoside (Cytarabine).

Antifolates are drugs which impair the function of folic acids. Many are used in cancer chemotherapy, some are used as antibiotics or antiprotozoal agents. A well known example is Methotrexate. This is a folic acid analogue, and owing to structural similarity with it binds and inhibits the enzyme dihydrofolate reductase (DHFR), and thus prevents the formation of tetrahydrofolate. Tetrahydrofolate is essential for purine and pyrimidine synthesis, and this leads to inhibited production of DNA, RNA and proteins (as tetrahydrofolate is also involved in the synthesis of amino acids serine and methionine). Other antifolates include, but are not limited to, trimethoprim, raltitrexed, pyrimethamine and pemetrexed.

Examples of chemotherapeutic agents above are not limiting and other agents can be loaded in Nanoparticules. Among others, ellipticine and harmine can be cited.

Ellipticine is a natural plant alkaloid product which was isolated from the evergreen tree of the Apocynaceae family. Ellipticine was found to have cytotoxic and anticancer activity (Dalton et al., Aust. J. Chem., 1967. 20, 2715). The ellipticine derivative hydroxylated in position 9 (9-hydroxyellipticinium) was found to have greater antitumoral activity than ellipticine on many experimental tumours (Le Pecq et al., Proc. Natl. Acad, Sci., USA, 1974, 71, 5078-5082). Researches were performed to identify an ellipticine derivative appropriate for human therapeutics and lead to the preparation of Celiptium, or N2-methyl-9-hydroxyellipticinium (NMHE), which has been used for the treatment of some human cancers, in particular for the treatment of bone metastasis of breast cancers. Other 9-hydroxy ellipticine derivatives, such as 2-(diethylamino-2-ethyl)-9-hydroxyellipticinium acetate, 2-(diisopropylamino-ethyl)-9-hydroxyellipticinium acetate and 2-(beta piperidino-2-ethyl)-9-hydroxyellipticinium, had been described for instance in the U.S. Pat. No. 4,310,667.

Harmine is a natural plant alkaloid product which was isolated from the *Peganum harmala* seeds. *Peganum harmala* (Zygophyllaceae) is a plant widely distributed in semi arid rangelands in the Central Asia, North Africa, Middle East and Australia. The pharmacologically active compounds of *P. harmala* are several alkaloids that are found especially in the seeds and the roots. These include 3-carbolines such as harmine, harmaline, harmol, harmalol and harman, and quinazoline derivatives: vasicine and vasicinone. *Peganum harmala* alkaloids were found to possess significant antitumour potential (Lamchouri and al., Therapie, 1999, 54(6):753-8). Proliferation of tumoral cells lines was significantly reduced. Harmine was reported to exhibit strong cytotoxicity against a number of human tumor cell lines (Ishida and al, Bioorg Mad Chem Lett, 1999, 9(23): 3319-24). Anticancer activity of harmol dimers has also been described for instance in the international patent WO2009047298.

In a preferred embodiment, the chemotherapeutic agent is an anthracycline, preferably selected from the group consisting of doxorubicin, daunorubicin, epirubicin, idarubicin, valrubicin, pirarubicin, zorubicin, aclarubicin, detorubicin, caminomycin, morpholinodoxorubicin, morpholinodaunorubicin, methoxymorpholinyldoxorubicin, any pharmaceutically acceptable salt thereof, and any combination thereof, more preferably doxorubicin or any pharmaceutically acceptable salt thereof.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine or epolamine, metal salts such as sodium, potassium, calcium, zinc or magnesium. For instance, a suitable salt of doxorubicin is the doxorubicin hydrochloride.

In a particular embodiment, the Nanoparticules used in the invention comprise at least one chemotherapeutic agent, preferably selected from among anthracyclines, at least one poly($C_1$-$C_{12}$ alkylcyanoacrylate), preferably a polyisohexylcyanoacrylate, and at least one cyclodextrin, preferably selected from the group consisting of hydroxypropyl-beta-cyclodextrin and randomly methylated-beta cyclodextrin, and mixtures thereof. In a particularly preferred embodiment, the Nanoparticules comprise doxorubicin, a polyisohexylcyanoacrylate and a hydroxypropyl-beta-cyclodextrin.

The chemotherapeutic agent is generally present at a concentration from about 0.01 to about 200 mg/g of Nanoparticules, preferably from about 1 to about 50 mg/g.

The proportion of cyclodextrin is in general from about 0.1 to about 70% by weight of Nanoparticules, preferably from about 1 to about 30%, more preferably from about 5 to about 20%. The proportion of the chemotherapeutic agent and the proportion of cyclodextrin are independent from one another.

The proportion of poly(alkylcyanoacrylate) polymer is in general from about 1 to about 25% by weight of Nanoparticules, preferably from about 5 to about 15%.

In a particular embodiment, the Nanoparticules comprise a chemotherapeutic agent at a concentration from 0.01 to 200 mg/g of Nanoparticules, from 0.1 to 70% w/w of cyclodextrin and from 1 to 25% w/w of poly(alkylcyanoacrylate), preferably of polyisohexylcyanoacrylate.

As used in this specification, the term "about" refers to a range of values ±10% of the specified value. For instance, "about 1" means from 0.9 to 1.1 when 10% is considered and from 0.95 to 1.05 when 5% is considered. Where "about" is used in connection with numeric ranges, for example "about 1 to about 3", or "between about one and about three", preferably the definition of "about" given above for a number is applied to each number defining the start and the end of a range separately. Preferably, where "about" is used in connection with any numerical values, the "about" can be deleted.

The Nanoparticules used in the present invention may be prepared according any method known by the skilled person. Such a method is disclosed, for example, in the European patent EP 1 056 477 and its US equivalent U.S. Pat. No. 6,881,421.

In particular, the Nanoparticules may be prepared by a method comprising the steps of
a) preparing, in an acid aqueous, a complex of the chemotherapeutic agent with cyclodextrin;
b) gradually adding the alkylcyanoacrylate monomer, preferably the isohexylcyanoacrylate monomer, in the solution obtained at step (a); and
c) conducting polymerization of this monomer, optionally in the presence of one or more surfactant and/or stabilising agents.

Preferably, the polymerization is anionic but may also be inducible by other agents, in particular by photochemical agents. In a particular embodiment, the polymerization is conducted in presence of a surfactant agent such as poloxamer or dextran (such as dextran 70,000) or other non ionic surfactive agents (like polysorbate, sorbitan esters or others). Poloxamers are preferred, such as poloxamer 407, poloxamer 401, poloxamer 237, poloxamer 338, poloxamer 331, poloxamer 231, or poloxamer 188 (also named Pluronic® F68). Poloxamer 188 is more preferred.

The size of the Nanoparticules is from about 50 to about 300 nm, preferably from about 100 to about 300 nm, more preferably about 200 nm. The size of these Nanoparticules is essentially related to the concentration of the cyclodextrin.

Nanoparticules as described above are administered in the form of a pharmaceutical composition comprising said Nanoparticules and at least one pharmaceutically acceptable excipient.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

The pharmaceutical composition comprising said Nanoparticules is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. In particular, possible pharmaceutical compositions include those suitable for intravenous, intra-arterial and intra-tumoral administration. For these formulations, conventional excipient can be used according to techniques well known by those skilled in the art. Such compositions for parenteral administration are generally physiologically compatible sterile solutions or suspensions which can optionally be prepared immediately before use from solid or lyophilized form. Adjuvants such as a local anaesthetic, preservative and buffering agents can be dissolved in the vehicle and a surfactant or wetting agent can be included in the composition to facilitate uniform distribution of the Nanoparticules.

The pharmaceutical composition may comprise one or several types of Nanoparticules, comprising one or several different chemotherapeutic agents.

In addition to Nanoparticules as described above, the pharmaceutical composition may further comprise at least one additional active substance, such as another chemotherapeutic agent included in Nanoparticules.

The Nanoparticules used in the present invention are to be administered to a patient in need thereof to provide a therapeutically effective amount of the chemotherapeutic agent(s).

As used herein, the term "patient" refers to either an animal, such as a valuable animal for breeding, company or preservation purposes, or preferably a human or a human child, which is afflicted with, or has the potential to be afflicted cancer.

As used herein, a "therapeutically effective amount" refers to an amount of a compound which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment. The amount of Nanoparticules to be administered has to be determined by standard procedure well known by those of ordinary skill in the art. In particular, physiological data of the patient (e.g. age, size, and weight), the type and localisation of cancer, the nature of the chemotherapeutic agent have to be taken into account to determine the appropriate dosage.

In a particular embodiment, the chemotherapeutic agent is doxorubicin and the Nanoparticules are to be administered in an amount providing a dosage of doxorubicin from about 10 to about 75 mg/m$^2$, preferably from about 10 to about 60 mg/m$^2$, preferably from about 10 to about 45 mg/m$^2$, more preferably from about 10 to about 30 mg/m$^2$, from about 20 to about 30 mg/m$^2$. More preferably, the dosage of doxorubicin may be about 20 mg/m$^2$ or 30 mg/m$^2$.

The body surface area of a patient can easily be calculated by the skilled person from the body weight and height of the patient (e.g. body weight of about 65 kg corresponds to a body surface of about 1.8 m$^2$).

The inventors have herein demonstrated that intravenous or intra-arterial infusion of Nanoparticules for at least 2 hours allows to strongly reduce toxicological side effects of the treatment then dramatically increases the benefit/risk ratio.

Consequently, the Nanoparticules as described above are to be administered by intravenous or intra-arterial infusion for at least 2 hours, preferably for between 2 and 24 hours, more preferably for between 4 and 12 hours, and even more preferably for about 6 hours. The volume to be administered and the flow rate may be easily determined by the skilled person in order to infuse a therapeutically effective amount of Nanoparticules in at least two hours.

The Nanoparticules may be administered in more than one treatment. They may be administered in one or several further treatment cycles (after initial treatment, i.e. the first infusion) with an interval of about two to about eight weeks between treatments, preferably about three to about four weeks, more preferably about four weeks. In an embodiment, administration of the Nanoparticules occurs on the first day of a 2-weekly to 8-weekly cycle. In a particular embodiment, the Nanoparticules are administered in two or three treatments with an interval between each treatment of two to about eight weeks, preferably about four weeks. Doses administered in each treatment cycle may be identical or different. The number of treatment cycles and the doses to be administered may be determined by the physician according to the physiological state of the patient, and the evolution of the disease. In another preferred embodiment, one or several further treatment cycles as described above are given during one to 28 month.

As used herein, the term "intravenous administration" ("IV") refers to the infusion of liquid substances directly into a vein.

This term refers to any type of intravenous access devices. In particular, this term refers to hypodermic needle. It is the simplest form of intravenous access by passing a hollow needle through the skin directly into the vein. This needle can be connected directly to a syringe or may be connected to a length of tubing and thence whichever collection or infusion system is desired.

The most convenient site is often the arm, especially the veins on the back of the hand, or the median cubital vein at the elbow, but any identifiable vein can be used.

It also refers to peripheral cannula. A Peripheral IV line (PVC or PIV) consists of a short catheter (a few centimeters long) inserted through the skin into a peripheral vein (any vein not inside the chest or abdomen). This is usually in the form of a cannula-over-needle device, in which a flexible plastic cannula comes mounted on a metal trocar. Once the tip of the needle and cannula are located in the vein, the trocar is withdrawn and discarded and the cannula advanced inside the vein to the appropriate position and secured.

Any accessible vein can be used although arm and hand veins are used most commonly, with leg and foot veins used to a much lesser extent.

This term can also refer to central IV lines flow through a catheter with its tip within a large vein, usually the superior vena cava or inferior vena cava, or within the right atrium of the heart. This has several advantages over a peripheral IV:

It can deliver fluids and medications that would be overly irritating to peripheral veins because of their concentration or chemical composition. These include some chemotherapy drugs and total parenteral nutrition.

Medications reach the heart immediately, and are quickly distributed to the rest of the body.

There are several types of central IVs, depending on the route that the catheter takes from the outside of the body to the vein.

It also can refer to peripherally inserted central catheter (PICC) which are used when intravenous access is required over a prolonged period of time or when the material to be infused would cause quick damage and early failure of a peripheral IV and when a conventional central line may be too dangerous to attempt. Typical uses for a PICC include: long chemotherapy regimens, extended antibiotic therapy, or total parenteral nutrition.

The PICC line is inserted through a sheath into a peripheral vein, usually in the arm, and then carefully advanced upward until the catheter is in the superior vena cava or the right atrium.

The intravenous access devices can also be central venous lines. There are several types of catheters that take a more direct route into central veins. These are collectively called central venous lines. In the simplest type of central venous access, a catheter is inserted into a subclavian, internal jugular, or (less commonly) a femoral vein and advanced toward the heart until it reaches the superior vena cava or right atrium.

This term also refers to implantable ports (often referred to by brand names such as Port-a-Cath or MediPort) which are a central venous line that does not have an external connector; instead, it has a small reservoir that is covered with silicone rubber and is implanted under the skin. Medication is administered intermittently by placing a small needle through the skin, piercing the silicone, into the reservoir. It is possible to leave the ports in the patient's body for years; if this is done however, the port must be accessed monthly.

The delivery of therapeutic agents intra-arterially requires selective vascular catheterization, which is accomplished by tailoring the catheter configuration to the vascular anatomy.

As used herein, the term "intra-arterial administration" refers to the infusion of liquid substances directly into an artery. This term refers to any type of intra-arterial access devices.

This term can refers to an arterial line, or art-line, or a-line, which is a thin catheter inserted into an artery. An arterial line is usually inserted in the wrist (radial artery); but can also be inserted into the elbow (brachial artery), groin (femoral artery), foot (dorsalis pedis artery).

This term can refers to syringe driver or syringe pump which is a small infusion pump (some include infuse and withdraw capability), used to gradually administer small amounts of fluid to a patient or for use in chemical and biomedical research. Syringe drivers are also useful for delivering medications over several minutes. In the case of a medication which should be slowly pushed in over the course of several minutes, this device saves staff time and reduces errors.

This term also refers to the Catheter-Port Systems. To facilitate the long-term administration of chemotherapeutic agents, percutaneoulsy implantable catheter-port systems have been developed for long-term use. These systems allow easy and repetitive puncture in infusion therapy without causing much harm to the vessels, and their use is comfortable for the patient. Catheter system can be surgically implanted in the gastro duodenal artery or via the subclavian, axillary, or brachial arteries into the common hepatic artery or in the femoral artery. The configuration of the catheter used depended on the vascular anatomy of the patient. The standard catheter-port device consisted of a titanium port reservoir with a silicone rubber membrane at the puncture site and a lateral stem to slip the silicone catheter over. The connection between the silicone catheter and the diagnostic angiographic catheter was reinforced with a small metallic cannula (Liver Intraarterial Chemotherapy: Use of the Femoral Artery for Percutaneous Implantation of Catheter-Port Systems, Karin Anna Herrmann et al. April 2000 Radiology, 215, 294-299).

This term can also refers to intra-arterial chemotherapy (IAC) which is an innovative chemotherapy method used to treat liver cancer, as well as cancers that have spread to the liver, such as metastatic pancreatic cancer. IAC is used to send chemotherapy directly into a tumor through a catheter placed in the artery. The goal of IAC is to concentrate the drug inside the tumor and minimize the exposure to healthy tissues. During IAC, a thin catheter is inserted through the femoral artery in the right leg. An angiogram is performed to obtain a "roadmap" of the arteries. This roadmap is then used to insert a line into the hepatic artery, which is the main blood vessel that delivers blood to the liver. Using dye from a syringe to make sure the line is in the correct position, the chemotherapy drug or drugs are injected directly into the artery.

As used herein, the term "cancer" refers to the presence of cells possessing characteristics typical of cancer-causing cells, such as uncontrolled proliferation, immortality, metastatic potential, rapid growth and proliferation rate, and certain characteristic morphological features. This term refers to any type of malignancy (primary or metastases). In particular, this term refers to any malignant proliferative cell disorders such as solid tumor or hematopoietic tumor, including carcinoma, sarcoma, lymphoma, stem cell tumor, blastoma. Preferably, the cancer is selected from the group consisting of hepatic cancer, in particular hepatocellular carcinoma, acute lymphoblastic leukemia, acute myeloblastic leukemia, chronic myelogenous leukemia, Hodgkin's disease, diffuse large B-cell lymphoma, lung cancer, in particular small cell lung cancer, colorectal cancer, pancreas cancer, breast cancer, ovary cancer, uterine cancer, cervix cancer, head and neck cancer, brain cancer, blade cancer, multiple myeloma, neuroblastoma, Edwing's sarcoma, osteosarcoma, soft tissue sarcoma, thyroid cancer, prostate cancer, stomach cancer, nephroblastoma, Kaposi's sarcoma, and non-Hodgkins lymphoma. More preferably, the cancer is selected from the group consisting of hepatocellular carcinoma, acute lymphoblastic leukemia, acute myeloblastic leukemia, chronic myelogenous leukemia, Hodgkin's disease, diffuse large B-cell lymphoma, small cell lung cancer, breast cancer, ovary cancer, blade cancer, multiple myeloma, neuroblastoma, Edwing's sarcoma, osteosarcoma, soft tissue sarcoma, thyroid cancer, prostate cancer, stomach cancer, nephroblastoma, Kaposi's sarcoma, and non-Hodgkins lymphoma. In a preferred embodiment, the cancer is a hepatic cancer, preferably a hepatocellular carcinoma.

In a particular embodiment, the Nanoparticules comprise doxorubicin, polyisohexylcyanoacrylate, hydroxypropyl-beta-cyclodextrin and/or randomly methylated-beta cyclodextrin, for use for treating a hepatocellular carcinoma, wherein the Nanoparticules are to be administered by intravenous or intra-arterial infusion for at least 2 hours.

The following examples are given for purposes of illustration and not by way of limitation.

EXAMPLES

Example 1

Manufacturing of Nanoparticules Loaded with Doxorubicin (Nanoparticules Loaded with Doxorubicin)

Nanoparticules loaded with Doxorubicin product developed is presented as a sterile lyophilisate for injectable suspension that contains doxorubicin hydrochloride as active ingredient and other excipients including the Nanoparticules polymer, PIHCA. The drug-loaded Nanoparticules are obtained by aqueous emulsion polymerisation of isohexylcyanoacrylate (IHCA) monomer dropped in the bulk solution containing the active ingredient doxorubicin and the other excipients (P. Couvreur, B. Kanté, M. Roland, P. Guiot, P. Baudhuin, P. Speiser, J. Pharm. Pharmacol., 1979, 31, 331). At the end of polymerisation, a stable suspension of Nanoparticules entrapping doxorubicin is obtained. The Nanoparticules mean size is comprised between 100 nm to 300 nm. The Nanoparticules suspension is then filtered and aseptically filled in glass vials before freeze-drying. Nanoparticules loaded with Doxorubicin freeze-dried product must be kept protected from light and humidity and stored in a refrigerator between 2° C.-8° C., for stability purposes.

Raw Materials

For 100 ml of total volume of polymerization media:

| Excipients | Quantity (gram) |
| --- | --- |
| Anhydrous glucose | 5 |
| Lactose | 0.4 |
| Poloxamer 188 | 1 |
| Hydroxypropyl-beta Cyclodextrin | 0.5 |
| $H_2O$ | qsp 100 ml |
| Anhydrous citric acid (1M) | qsp ph = 3 to 4 |

Method for Preparing 100 Ml of Polymerization Medium (pH Comprises Between 3 and 4)
  Excipients are added to about 75 ml of $H_2O$.
  Excipients are dissolved with magnetic stirring bar
  Completion with $H_2O$ until obtaining a 100 ml volume.
  pH is eventually adjusted with citric acid 1M
Method for Preparing Nanoparticules Loaded with Doxorubicin (5 Ml Batches)
  In a 10 ml flask:
  Add 4,625 ml of polymerization media
  Add 375 µl of doxorubicin solution at 10 mg/ml
  Mix with magnetic stirring bar
  Add 50 µl of pure IHCA solution (density of IHCA=0,980)—Let polymerization occurs up to 2 h30 period of time or more, under magnetic stirring and room temperature
  Filtration onto 2 µm filters Example 2

Assessment of a Model of Adverse Effects Induced after a Single iv Bolus Injection of Nanoparticles Loaded with Doxorubicin in Healthy Wistar Rats Described above randomized, multicentre phase 2-3 evaluating Nanoparticules loaded with Doxorubicin in Advanced HepatoCellular Carcinoma by intraarterial route, has been stopped in 2008 for severe to fatal respiratory distress in treated patients.

The aim of the present in vivo study was to establish and assess a rat model able to induce toxicological signs and lung injuries similar to severe pulmonary adverse events observed in said clinical trial. Inventors studied the toxicological effects of a single bolus IV injection of a clinical batch of Nanoparticules loaded with Doxorubicin on healthy Wistar rats at early (24 h, 48 h, 72 h) and late (7 days) monitoring times.

The dose levels of 5, 7.5 and 10 mg/kg were chosen according to previous in vivo studies, they respectively correspond to 30 mg/m2, 45 mg/m2 and 60 mg/m2 human doses.

Drug Administration

The study involved finally 123 male Wistar rats.

Rats were weighted and distributed according to their individual body weight to form 5 groups of 24 rats the day of IV treatment.

The IV dose was administered as a bolus at a rate of about 1000 µl/min or 3700 µg Doxorubicin-HCl/min in the penis vein under light isoflurane anaesthesia.

The rats from groups 1 to 4 received a single IV injection of Nanoparticules loaded with Doxorubicin (batch BA003-07C001PH) at 5 mg/kg equivalent Doxorubicin HCl (Q1Dx1). Drug suspension was administered according to the body weight of rat determined just before the administration, so as to administer a dose volume of 340 µl of a 3.71 mg/ml suspension to a 250 g rat.

The rats from groups 5 to 8 received a single IV injection of Nanoparticules loaded with Doxorubicin (batch BA003-07C001PH) at 7.5 mg/kg equivalent Doxorubicin HCl (Q1Dx1). Drug suspension was administered according to the body weight of rat determined just before the administration, so as to administer a dose volume of 510 µl of a 3.71 mg/ml suspension to a 250 g rat.

The rats from groups 9 to 12 received a single IV injection of Nanoparticules loaded with Doxorubicin (batch BA003-07C001PH) at 10 mg/kg equivalent Doxorubicin HCl (Q1Dx1). Drug suspension was administered according to the body weight of rat determined just before the administration, so as to administer a dose volume of 670 µl of a 3.71 mg/ml suspension to a 250 g rat.

The rats from groups 13 to 16 received a single IV injection of Doxorubicin at 7.5 mg/kg equivalent Doxorubicin HCl (Q1Dx1). Solution was administered according to the body weight of rat determined just before the administration, so as to administer a dose volume of 530 µl of a 3.55 mg/ml suspension to a 250 g rat.

The rats from groups 17 to 20 (Excipient control group) received a single IV administration of the same volume of Excipient solution that 10 mg/kg of Nanoparticules loaded with Doxorubicin treated group. Solution was administered according to the body weight of rat determined just before the administration, so as to administer a dose volume of 670 µl solution to a 250 g rat.

The rats from group 21 (Untreated control group) received no treatment.

Treatment allocation was decided at random and was as disclosed in Table 2.

TABLE 2

Treatment allocation of rats at D 0

| Group | No of animals per group | Treatment | Route | Dose mg/kg, equivalent Dox-HCl | Quantity of equivalent Dox-HCl (mg, rat weight = 250 g) | Dose mg/kg, equivalent NP-PIHCA | Treatment schedule | Scheduled day of euthanasia |
|---|---|---|---|---|---|---|---|---|
| 1 | 6 | Nanoparticles | IV | 5 | 1.250 | 66.50 | Q1Dx1 | D 1 |
| 2 | 6 | Nanoparticles | IV | 5 | 1.250 | 66.50 | Q1Dx1 | D 2 |
| 3 | 6 | Nanoparticles | IV | 5 | 1.250 | 66.50 | Q1Dx1 | D 3 |
| 4 | 6 | Nanoparticles | IV | 5 | 1.250 | 66.50 | Q1Dx1 | D 7 |
| 5 | 6 | Nanoparticles | IV | 7.5 | 1.875 | 99.75 | Q1Dx1 | D 1 |
| 6 | 6 | Nanoparticles | IV | 7.5 | 1.875 | 99.75 | Q1Dx1 | D 2 |
| 7 | 6 | Nanoparticles | IV | 7.5 | 1.875 | 99.75 | Q1Dx1 | D 3 |
| 8 | 6 | Nanoparticles | IV | 7.5 | 1.875 | 99.75 | Q1Dx1 | D 7 |
| 9 | 6 | Nanoparticles | IV | 10 | 2.500 | 133.00 | Q1Dx1 | D 1 |
| 10 | 6 | Nanoparticles | IV | 10 | 2.500 | 133.00 | Q1Dx1 | D 2 |
| 11 | 6 | Nanoparticles | IV | 10 | 2.500 | 133.00 | Q1Dx1 | D 3 |
| 12 | 5 | Nanoparticles | IV | 10 | 2.500 | 133.00 | Q1Dx1 | D 7 |
| 13 | 6 | Doxorubicin | IV | 7.5 | 1.875 | — | Q1Dx1 | D 1 |

TABLE 2-continued

Treatment allocation of rats at D 0

| Group | No of animals per group | Treatment | Route | Dose mg/kg, equivalent Dox-HCl | Quantity of equivalent Dox-HCl (mg, rat weight = 250 g) | Dose mg/kg, equivalent NP-PIHCA | Treatment schedule | Scheduled day of euthanasia |
|---|---|---|---|---|---|---|---|---|
| 14 | 6 | Doxorubicin | IV | 7.5 | 1.875 | — | Q1Dx1 | D 2 |
| 15 | 6 | Doxorubicin | IV | 7.5 | 1.875 | — | Q1Dx1 | D 3 |
| 16 | 6 | Doxorubicin | IV | 7.5 | 1.875 | — | Q1Dx1 | D 7 |
| 17 | 6 | Excipient Control | IV | — | — | — | Q1Dx1 | D 1 |
| 18 | 6 | Excipient Control | IV | — | — | — | Q1Dx1 | D 2 |
| 19 | 6 | Excipient Control | IV | — | — | — | Q1Dx1 | D 3 |
| 20 | 6 | Excipient Control | IV | — | — | — | Q1Dx1 | D 7 |
| 21 | 4 | Untreated Control | — | — | — | — | — | — |

Results

First, inventors observed at the highest doses of Nanoparticules loaded with Doxorubicin (7.5 mg/kg and 10 mg/kg) an important number of deaths during the first two days of follow up. These deaths were closely associated with lung injuries characterized by:
- macroscopic modifications of the lungs,
- presence of exudates
- increase in lung weight
- oedemas, alveolitis Neither mortality, nor lung injuries were observed in the group treated with IV bolus injection of Nanoparticules loaded with Doxorubicin 5 mg/kg, of free doxorubicin at 7.5 mg/kg or with the Nanoparticules excipients.

Thus, this study allows to establish rat model of lung injury after IV bolus administration of Nanoparticules loaded with Doxorubicin and to study the prevention of these serious adverse events.

For further investigation in the prevention of these adverse events, the dose of 7.5 mg/kg was chosen as the dose allowing to follow the lung injury until Day 2 with limited unscheduled deaths in comparison to the 10 mg/kg dose.

Example 3

Investigation of the Impact of Administration Speed on the Tolerance of a Single IV Injection of Nanoparticules Loaded with Doxorubicin in Healthy Wistar Rats To investigate respiratory adverse events observed in clinical trials with Nanoparticules loaded with Doxorubicin, a rat model of lung injury has been set up. Previous studies (Example2) showed that IV bolus administration of Nanoparticules loaded with Doxorubicin at the dose of 7.5 mg/kg to healthy Wistar rats induced major toxicological effects, with lung injury and respiratory distress. Moreover, 48 h after the injection, in 63% of injected rats, mortality was observed correlated with major lung injury.

The aim of the present study was to compare the tolerance of Nanoparticules loaded with Doxorubicin (clinical batch BA003-07C001PH) at the same dose level of 7.5 mg/kg injected intravenously by a single bolus injection (1000 µl/min or 3660 µg Doxorubicin-HCl/min) or by a 2 hours perfusion (4.3 µl/min or 15.6 µg Doxorubicin-HCl/min). The dose level of 5 mg/kg (corresponding to 30 mg/m2 in human) administered by a single bolus IV injection (1000 µl/min or 3660 µg Doxorubicin-HCl/min) was chosen as safe bolus dose based on results of the previous study: no mortality and no lung injuries were observed at this dose. Rat euthanasia was performed 48 h after the treatment, according to scheme appearance of toxicological effects observed in previous studies.

Drug Administration

The study involved 32 male Wistar rats.

Rats were weighted and distributed according to their individual body weight to form 5 groups of 6 rats for IV bolus or 8 rats for IV perfusion the day of the first IV treatment.

The IV injection was performed under light isoflurane anesthesia via the femoral vein in the case of perfusion at a rate of 4.3 µl/min (corresponding to 15.6 µg (Dox-HCl)/min) for a 250 g rat (3.66 mg/ml suspension) and by the penis vein in the case of bolus injection at a rate of about 1000 µl/min (corresponding to 3660 µg (Dox-HCl)/min).

To determine the real administered dose, each syringe and catheter was weighted before and after treatment.

The rats from group 1 received a single IV perfusion injection of Nanoparticules loaded with Doxorubicin (batch BA003-07C001PH) at 7.5 mg/kg equivalent Doxorubicin HCl (Q1Dx1). Drug suspension was administered according to the body weight of rat determined just before the administration, so as to administer a dose volume of 2.05 ml/kg of a 3.66 mg/ml suspension. The perfusion rate was defined as 4.3 µl/min (15.6 µg (Dox-HCl)/min) for a 250 g rat (2 h perfusion).

The rats from group 2 received a single bolus IV injection of Nanoparticules loaded with Doxorubicin (batch BA003-07C001PH) at 7.5 mg/kg equivalent Doxorubicin HCl (Q1Dx1). Drug suspension was administered according to the body weight of rat determined just before the administration, so as to administer a dose volume of 2.05 ml/kg of a 3.66 mg/ml suspension. The injection rate was defined as 1000 µl/min (3660 µg (Dox-HCl)/min), The rats from group 3 received a single IV bolus injection of Nanoparticules loaded with Doxorubicin (batch BA003-07C001PH) at 5 mg/kg equivalent Doxorubicin HCl (Q1Dx1). Drug suspension was administered according to the body weight of rat determined just before the administration, so as to administer a dose volume of 1.37 mL/kg of a 3.66 mg/mL suspension. The injection rate was defined as 1000 µl/min (3660 µg (Dox-HCl)/min).

The rats from group 4 (Excipient control group) received a single IV administration of the same volume of excipient solution that 7.5 mg/kg Nanoparticules loaded with Doxorubicin treated group. Solution was administered according to the body weight of rat determined just before the administration, so as to administer a dose volume of 2.05 ml/kg.

The rats from group 5 (Anesthesia/surgery control) were anesthetized and a catheter filled with saline solution and connected to a syringe of saline solution was inserted in the femoral vein. The rats were maintained under anesthesia during 2 hours after the surgery. Treatment allocation was decided according to their individual body weight as follows:

TABLE 3

Treatment allocation of rats at the day of administration

| Group | No of animals/ group | Treatment | Route | Dose mg/kg, equivalent Doxo HCl | Quantity of equivalent Doxo HCl (mg, rat weight = 250 g) | Dose mg/kg, equivalent NP-PIHCA | Treatment schedule |
|---|---|---|---|---|---|---|---|
| 1 | 8 | Nanoparticules BA003-07C001PH | IV, perfusion | 7.5 | 1.875 | 99.75 | Q1Dx1 |
| 2 | 6 | Nanoparticules BA003-07C001PH | IV, bolus | 7.5 | 1.875 | 99.75 | Q1Dx1 |
| 3 | 6 | Nanoparticules BA003-07C001PH | IV, bolus | 5 | 1.250 | 66.50 | Q1Dx1 |
| 4 | 6 | Excipient Control | IV, bolus | — | — | — | Q1Dx1 |
| 5 | 6 | Anesthesia/ Surgery control | — | — | — | — | — |

Results

Mortality

In 7.5 mg/kg Nanoparticules loaded with Doxorubicin IV bolus group, two rats over 6 were found dead at D1 after bolus injection and two rats were found dead at D2, corresponding to mortality rate of 4/6 treated rats (66.7%) at the end of the study.

In 7.5 mg/kg Nanoparticules loaded with Doxorubicin IV perfusion group, the first treated rat was found dead at D2 after treatment, corresponding to a mortality rate of 1/8 treated rats (12.5%) at the end of the study.

In 5 mg/kg Nanoparticules loaded with Doxorubicin IV bolus group, no mortality was observed until the end of the study.

In excipient control group and in anesthesia/surgery control group, no mortality was observed until the end of the study.

TABLE 4

Mortality follow up

| Treatment | | D1 | D2 | At the end of study |
|---|---|---|---|---|
| Nanoparticules 7.5 mg/Kg | Rat N° | 6 | 4 | 2 |
| | Death | 2/6 | 2/4 | 4/6 |
| | Mortality | 33.3% | 50.0% | 66.7% |
| Nanoparticules 7.5 mg/Kg IV perfusion | Rat N° | 8 | 8 | 7 |
| | Death | 0/8 | 1/8 | 1/8 |
| | Mortality | 0% | 12.5% | 12.5% |
| Nanoparticules 5 mg/Kg IV Bolus | Rat N° | 6 | 6 | 6 |
| | Death | 0/6 | 0/6 | 0/6 |
| | Mortality | 0% | 0% | 0% |
| Anesthesia/Surgery Control | Rat N° | 6 | 6 | 6 |
| | Death | 0/6 | 0/6 | 0/6 |
| | Mortality | 0% | 0% | 0% |
| Excipient Control IV Bolus | Rat N° | 6 | 6 | 6 |
| | Death | 0/6 | 0/6 | 0/6 |
| | Mortality | 0% | 0% | 0% |

Lungs Examination

Major lung injuries were observed in 7.5 mg/kg Nanoparticules loaded with Doxorubicin IV bolus treated group whether dead rats (2/2) or euthanatized rats (3/4). These physiological alterations were characterized by the presence of exudate in the thoracic cavity, the increase of lung weight and hemorrhagic lungs with dark dots.

In the 7.5 mg/kg Nanoparticules loaded with Doxorubicin IV perfusion treated group, the inventors observed exudate in the thoracic cavity of one rat: the rat N° 1 that was found dead at D2. Moreover, this rat showed hemorrhagic lungs. The inventors did not observe exudate in the thoracic cavity for the others rats of this group. However, they observed hemorrhagic lungs for rat N° 2 that showed a decrease of its general health status before euthanasia. It is to note that the colour of lungs of rats N° 3 and N° 4 was not uniform. The last 4 rats of this perfusion group of 8 animals did not show any lung alterations.

Inventors did not observe any exudate in the thoracic cavity and any macroscopic lung alterations in 5 mg/kg Nanoparticules loaded with Doxorubicin IV bolus treated group, in Excipient control group and anesthesia/surgery control group.

TABLE 5

Summary of macroscopic lung injury

| Treatment | Rat N° | Incidence of macroscopic injuries |
|---|---|---|
| Nanoparticules 7.5 mg/Kg IV Bolus | 6 | 5/6 |
| Nanoparticules 7.5 mg/Kg IV Perfusion | 8 | 2/8 |
| Nanoparticules 5 mg/Kg IV Bolus | 6 | 0/6 |
| Anesthesia/Surgery Control | 6 | 0/6 |
| Excipient Control | 6 | 0/6 |

Conclusion

Inventors previously described a rat model of lung injury after an IV bolus injection (1000 µl/min or 3660 µg Doxorubicin-HCl/min) of Nanoparticules loaded with Doxorubicin at the dose level of 7.5 mg/kg (Equivalent Human Dose—EHD—=45 mg/m2). Inventors observed, 48 h after the treatment a high mortality (62.5% of treated animals) and strong lung injury with exudates in the thoracic cavity, hemorrhagic lungs with dark dots and a significant increase of lung weight (98% vs control group).

In this study, Inventors first confirmed the pulmonary toxicity of an IV bolus injection (1000 µl/min or 3660 µg Doxorubicin-HCl/min) of Nanoparticules loaded with Doxorubicin at the dose level of 7.5 mg/kg, with similar lung macroscopic observations (exudates in the thoracic cavity, hemorrhagic lungs with dark dots), an increase of lung weight (116.6% vs control group, p=0.0038) and an associated mortality (66.7% of treated animals).

Moreover, the present study surprisingly showed that a slow perfusion rate of Nanoparticules loaded with Doxorubicin (2 h perfusion, 4.3 µl/min or 15.6 µg Doxorubicin-HCl/min) at the dose level of 7.5 mg/kg strongly reduced these toxicological side effects compared to a bolus IV injection at the same dose, 48 h after administration. Indeed, mortality was markedly reduced in perfusion group as 87.5% of rats were still alive 48 h after the treatment compared to 33.3% in bolus group at the same dose level. Macroscopic lung injuries were also reduced in perfusion group as only 2/8 rats showed hemorrhagic lungs whereas 5/6 rats showed normal lungs in bolus group at the same dose level. In the same way, the increase of lung weight was weaker and no significant in perfusion group compared to bolus group (75.4%).

Example 4

Histological Evaluation of Lung and Heart of Healthy Rats after a Single Intravenous Injection of Nanoparticules Loaded with Doxorubicin. Comparative Study Between IV Bolus and Perfusion Administration Previous studies showed that IV bolus administration of Nanoparticules loaded with Doxorubicin at the dose of 7.5 mg/kg to healthy Wistar rats induced major toxicological effects, with lung injury and respiratory distress. Moreover, in 63-67% of treated rats, mortality was observed within 48 h after the injection and was correlated with major lung injuries (example 2). Further investigations demonstrated that a slow IV administration of Nanoparticules loaded with Doxorubicin at the dose level of 7.5 mg/kg strongly reduced toxicological side effects compared to a bolus IV injection at the same dose. Neither mortality nor macroscopic lung injury were observed in perfusion group 48 h after the treatment compared to bolus group (87.5% of mortality and lung injury). The increase of lung weight was also significantly weaker in perfusion group (12%) compared to bolus group (166%). These studies also demonstrated that IV bolus injection of Nanoparticules loaded with Doxorubicin at a lower dose level of 5 mg/kg is safe and well tolerated without mortality or lung injury (example 3).

The major adverse effects reported in the field of drug-induced pulmonary toxicity are histological changes in the pulmonary parenchyma, the pleura, the airways, the pulmonary vascular system, and the mediastinum. Histological lesions consist in pulmonary changes such as alveolar damage, fibrosis and inflammatory infiltrate (Pereverzeva E et al., Influence of the formulation on the tolerance profile of nanoparticle-bound doxorubicin in healthy rats: focus on cardio- and testicular toxicity. Int J. Pharm. 2007, 337(1-2): 346-56. Perivascular oedema is known to be a major parameter in the assessment of lung toxicity, particularly in hypersensitivity (Tigani B et al., Resolution of the oedema associated with allergic pulmonary inflammation in rats assessed noninvasively by magnetic resonance imaging. British Journal of Pharmacology. 2003, 140, 2, 239-246). Few data are available in the literature for pulmonary toxicity of doxorubicin.

To further investigate the observed lung injuries, a histological evaluation after HES (Hematoxyline-Erythrosine-Safran) staining of lung and heart of Nanoparticules loaded with Doxorubicin injected intravenously in healthy Wistar rats was performed. Histological changes studied were in particular pulmonary perivascular oedema, alveolar damage, pleural inflammation and cellular infiltrates.

Treatment/Drug Administration

Two experiments have been conducted for this histological study.

For the two experiments, the IV injection was performed under light isoflurane anesthesia via the femoral vein in the case of perfusion at a rate of 4.3 µl/min and by the penis vein in the case of bolus injection at a rate of about 1000 µl/min. To determine the real administered dose, each syringe and catheter was weighted before and after treatment.

First Experiment (BA003-PKT-010Rv01)

The first experiment involved 16 male Wistar rats. Rats were weighted and distributed according to their individual body weight to form 5 groups of 3 rats for IV bolus, and 4 rats for IV perfusion.

The rats from group 1 received a single bolus IV injection of Nanoparticules loaded with Doxorubicin (clinical batch BA003-07C001PH) at 7.5 mg/kg equivalent Doxorubicin HCl. The injection rate was defined as 1000 µl/min (3660 µg (Dox-HCl)/min), The rats from group 2 received a single IV perfusion injection of Nanoparticules loaded with Doxorubicin (clinical batch BA003-07C001PH) at 7.5 mg/kg equivalent Doxorubicin HCl. The perfusion rate was defined as 4.3 µl/min (15.6 µg (Dox-HCl)/min) (2 h perfusion).

The rats from group 3 received a single IV bolus injection of Nanoparticules loaded with Doxorubicin (clinical batch BA003-07C001PH) at 5 mg/kg equivalent Doxorubicin HCl. The injection rate was defined as 1000 µl/min (3660 µg (Dox-HCl)/min).

The rats from group 4 (Anesthesia/surgery control) were anesthetized and a catheter filled with saline solution and connected to a syringe of saline solution was inserted in the femoral vein. The rats were maintained under anesthesia during 2 hours after the surgery.

The rats from group 5 (Excipient control group) received a single IV administration of the same volume of excipient solution that 7.5 mg/kg Nanoparticules loaded with Doxorubicin treated group.

Treatment allocation was performed as follow:

TABLE 6

Treatment allocation of rats at the day of administration

| Group | No of animals/ group | Treatment | Route | Dose mg/kg, equivalent Doxo HCl |
|---|---|---|---|---|
| 1 | 3 | Nanoparticulss loaded with Doxorubicin BA003-07C001PH | IV bolus | 7.5 |
| 2 | 4 | Nanoparticules loaded with Doxorubicin BA003-07C001PH | IV perfusion | 7.5 |
| 3 | 3 | Nanoparticules loaded with Doxorubicin BA003-07C001PH | IV bolus | 5 |
| 4 | 3 | Anesthesia/Surgery Control | — | — |
| 5 | 3 | Excipients Control | IV bolus | — |

Second Experiment (BA003-PKT-011Rv01)

The second experiment involved 14 male Wistar rats. Rats were weighted and distributed according to their individual body weight to form 4 groups of 4 rats for IV bolus, and 3 rats for IV perfusion.

The rats from group 1 received a single bolus IV injection of Nanoparticules loaded with Doxorubicin (clinical batch BA003-07C001PH) at 7.5 mg/kg equivalent Doxorubicin HCl. The injection rate was defined as 1000 µl/min (3660 µg (Dox-HCl)/min), The rats from group 2 received a single IV perfusion injection of Nanoparticules loaded with Doxorubicin (clinical batch BA003-07C001PH) at 7.5 mg/kg equivalent Doxorubicin HCl. The perfusion rate was defined as 4.3 µl/min (15.6 µg (Dox-HCl)/min) (2 h perfusion).

The rats from group 3 received a single IV bolus injection of Nanoparticules loaded with Doxorubicin (clinical batch BA003-07C001PH) at 5 mg/kg equivalent Doxorubicin HCl. The injection rate was defined as 1000 µl/min (3660 µg (Dox-HCl)/min).

The rats from group 4 (Excipient control group) received a single IV administration of the same volume of excipient solution that 7.5 mg/kg Nanoparticules loaded with Doxorubicin treated group.

Treatment allocation was performed as follow:

TABLE 7

Treatment allocation of rats at the day of administration

| Group | No of animals/ group | Treatment | Route | Dose mg/kg, equivalent Doxo HCl |
|---|---|---|---|---|
| 1 | 4 | Nanoparticules loaded with Doxorubicin BA003-07C001PH | IV bolus | 7.5 |
| 2 | 3 | Nanoparticules loaded with Doxorubicin BA003-07C001PH | IV perfusion | 7.5 |

TABLE 7-continued

Treatment allocation of rats at the day of administration

| Group | No of animals/ group | Treatment | Route | Dose mg/kg, equivalent Doxo HCl |
|---|---|---|---|---|
| 3 | 4 | Nanoparticules loaded with Doxorubicin BA003-07C001PH | IV bolus | 5 |
| 4 | 3 | Excipients Control | IV bolus | — |

Results

In both experiments, rats were euthanatized 48 hours after administration of the product by IV intravenous injection of an overdose of pentobarbital.

In the first experiment, 1/3 rat was found dead 24 h after 7.5 mg/kg IV bolus administration of Nanoparticules loaded with Doxorubicin and in the second experiment, 3/4 rats were found dead 24 hours or 48 hours after administration of 7.5 mg/kg IV bolus administration of Nanoparticules loaded with Doxorubicin. These observations have to be taken into account in the interpretation of the following histological observations.

In these two experiments testing intravenous injection of a clinical batch of Nanoparticules loaded with Doxorubicin in healthy Wistar rats, histological changes were observed, consisting in pulmonary perivascular oedema of variable intensity, occasional alveolar damage and slight pleural inflammation. The main feature observed in treated animals was an enlargement of the perivascular area consisting in an oedematous aspect.

Major pulmonary and cardiac damages were observed in the group receiving 7.5 mg/kg of Nanoparticules loaded with Doxorubicin at a bolus rate of about 1000 µL/min (or 3700 µg Doxorubicin-HCl/min) having caused the death of the animals. A major perivascular oedema was observed in 7.5 mg/kg bolus treated group: an increase of a ratio of 21.8 ($p=0.0065$) was observed in this group compared to control group.

The 7.5 mg/kg dose, when administered through a perfusion procedure at a rate of about 4.3 µL/min (or 15.6 µg Doxorubicin-HCl/min), induced mild or moderate pulmonary histological lesions and no cardiac lesions as opposed to the same dose level administered as a bolus injection.

The animals in the 5 mg/kg Nanoparticules loaded with Doxorubicin IV bolus group showed only mild pulmonary lesions. Pulmonary perivascular oedema was similar in 5 mg/kg bolus group and 7.5 mg/kg perfusion group and strongly reduced compared to 7.5 mg/kg bolus treated group.

Altogether, these results demonstrated that the reduction of the infusion rate of Nanoparticules loaded with Doxorubicin markedly decreased the incidence of fatal respiratory distress in healthy rats mainly characterized by a pulmonary perivascular oedema.

Example 5

Investigation of Potential Delayed Toxicological Effects of a Single IV Perfusion of Nanoparticules Loaded with Doxorubicin in Healthy Wistar Rats A 2-hour IV perfusion of Nanoparticules loaded with Doxorubicin (4.2 µL/min or 15.6 µg Doxorubicin-HCl/min for a 3.7 mg/mL suspension) was shown to induce an important decrease of the toxicological effects at this dose level, when comparing to a single bolus IV injection. A decrease of mortality was observed, with 79% of dead rats two days after the treatment in bolus group versus 6.7% in perfusion group. Moreover, a marked reduction of lung injuries was observed two days after the perfusion treatment (examples 3 and 4).

In these studies, euthanasia was always performed two days after the administration of Nanoparticules loaded with Doxorubicin whether in bolus treated group or perfusion treated group.

The aim of the present study is to investigate potential delayed toxicological effects after a 2 h-perfusion of Nanoparticules loaded with Doxorubicin. In this way, rats treated by a perfusion of Nanoparticules loaded with Doxorubicin at the dose level of 7.5 mg/kg will be euthanatized seven days after the treatment, compared to rats euthanatized after 48 h as performed in previous studies.

Treatment Drug/Administration

The study involved 34 male Wistar rats.

Rats were weighted and distributed to form 5 groups of 6 to 8 rats. The IV injection was performed under light isoflurane anaesthesia via the femoral vein in the case of a 2 h perfusion of a suspension at 3.69 mg/mL at a rate of 4.2 µL/min or 15.6 µg Doxorubicin HCl/min for a 250 g rat. In the case of the bolus injection via the penis vein, the injection rate was about 1000 µL/min or 3660 µg Doxorubicin HCl/min.

To determine the real administered dose, each syringe and catheter was weighted before and after treatment.

- The rats from group 1 will receive a single IV bolus injection of Nanoparticules loaded with Doxorubicin (batch BA003-07C001PH) at 7.5 mg/kg equivalent Doxorubicin HCl. Drug suspension was administered according to the body weight of rat determined just before the administration, so as to administer a dose volume of 2.04 mL/kg of a 3.69 mg/mL suspension. The injection rate was defined as 1000 µL/min or 3660 µg Doxorubicin HCl/min.
- The rats from group 2 received a single IV perfusion of Nanoparticules loaded with Doxorubicin (batch BA003-07C001PH) at 7.5 mg/kg equivalent Doxorubicin HCl. Drug suspension was administered according to the body weight of rat determined just before the administration, so as to administer a dose volume of 2.04 mL/kg of a 3.69 mg/mL suspension. The perfusion rate was defined as 4.2 µL/min or 15.6 µg Doxorubicin HCl/min for a 250 g rat (2 h perfusion). Rats were euthanatized 48 h after the treatment.
- The rats from group 3 received a single IV perfusion of Nanoparticules loaded with Doxorubicin (batch BA003-07C001PH) at 7.5 mg/kg equivalent Doxorubicin HCl. Drug suspension was administered according to the body weight of rat determined just before the administration, so as to administer a dose volume of 2.04 mL/kg of a 3.69 mg/mL suspension. The perfusion rate was defined as 4.2 µL/min or 15.6 µg Doxorubicin HCl/min for a 250 g rat (2 h perfusion). Rats were euthanatized 7 days after the treatment.
- The rats from group 4 (Excipient control group) received a single IV administration of the same volume of Excipient solution that 7.5 mg/kg Nanoparticules loaded with Doxorubicin treated group. Solution was administered according to the body weight of rat determined just before the administration, so as to administer a dose volume of 2.04 mL/kg. The injection rate was defined as 1000 µL/min. Rats were euthanatized 48 h after the treatment.
- The rats from group 5 (Excipient control group) received a single IV administration of the same volume of Excipient solution that 7.5 mg/kg Nanoparticules loaded with Doxorubicin treated group. Solution was administered according to the body weight of rat determined just before the administration, so as to administer a dose volume of 2.04 mL/kg. The injection rate was defined as 1000 µL/min. Rats were euthanatized 7 days after the treatment.

Treatment allocation was performed as follows:

TABLE 8

Treatment allocation of rats the day of administration

| Group | No of animals per group | Treatment | Route | Dose mg/kg, equivalent Dox-HCl | Quantity of equivalent Dox-HCl (mg, rat weight = 250 g) | Dose mg/kg, equivalent PIHCA | Euthanasia |
|---|---|---|---|---|---|---|---|
| 1 | 6 | Nanoparticules loaded with Doxorubicin BA003-07C001PH | IV, bolus | 7.5 | 1.875 | 99.75 | D 2 |
| 2 | 8 | Nanoparticules loaded with Doxorubicin BA003-07C001PH | IV, perfusion | 7.5 | 1.875 | 99.75 | D 2 |
| 3 | 8 | Nanoparticules loaded with Doxorubicin BA003-07C001PH | IV, perfusion | 7.5 | 1.875 | 99.75 | D 7 |
| 4 | 6 | Excipient Control | IV, bolus | — | — | — | D 2 |
| 5 | 6 | Excipient Control | IV, bolus | — | — | — | D 7 |

Mortality

In bolus group, three rats dead 24 h after the treatment (50% of injected rats) and one rat was found dead 48 h after the treatment, corresponding to a mortality rate of 66.7% at the end of the monitoring.

In the perfusion group, two rats dead at the end of the perfusion and one rat was found dead 24 h after the treatment. The mortality rate was about 20% at the end of the monitoring at D7 considering all rats infused at D0.

No mortality was observed in Excipient control group.

TABLE 9

Mortality follow-up during the study for Nanoparticules loaded with Doxorubicin treated groups (NA = Not applicable)

| Treatment | | D 0 | D 1 | D 2 | D 7 | At the end of the follow-up |
|---|---|---|---|---|---|---|
| Nanoparticules loaded with Doxorubicin 7.5 mg/kg iv bolus | Number of rats | 6 | 6 | 3 | NA | 2 |
| | Death | 0/6 | 3/6 | 1/3 | NA | 4/6 |
| | Mortality (%) | 0 | 50 | 33.3 | NA | 66.7 |
| Nanoparticules loaded with Doxorubicin 7.5 mg/kg iv perfusion | Number of rats | 16 | 13 | 12 | 7 | 7 |
| | Death | 2/15* | 1/13 | 0/12 | 0/7 | 3/15 |
| | Mortality (%) | 13.3 | 7.7 | 0 | 0 | 20 |

*Withdrawal of rat n°13 of Nanoparticules loaded with Doxorubicin perfusion group from the follow-up because of a drug outflow from the catheter during the infusion time at D 0.

Macroscopic Lungs Examination

Major lung injuries were observed in 7.5 mg/kg IV bolus treated group whether dead rats or one of the two surviving rats (5/6 rats). These physiological alterations were characterized by the presence of fluid in the thoracic cavity, the increase of lung weight, hemorrhagic lungs and/or lungs with dark dots.

We did not observe any exudate in the thoracic cavity in 7.5 mg/kg Nanoparticules loaded with Doxorubicin IV perfusion group. Nevertheless, two rats showed changes in lung colour, as rat N° 12 dead at D1 (with dark and hemorrhagic lungs) and rat N° 4 euthanatized at D7 (clear lungs with dark dots).

It is to note that rats in Excipient control group showed lungs with not uniform colour compared to the previous studies.

TABLE 10

Summary of incidence of macroscopic lung injuries

| Treatment | Number of rats | Incidence of macroscopic lung injuries |
|---|---|---|
| Nanoparticules loaded with Doxorubicin 7.5 mg/kg iv bolus | 6 | 5/6 |
| Nanoparticules loaded with Doxorubicin 7.5 mg/kg iv perfusion | 15 | 2/15 |
| Excipient control | 12 | 0/12 |

Lung Weight

The mean lung weight of each Nanoparticules loaded with Doxorubicin treated group was compared to the mean lung weight of Excipient control group.

The increase of lung weight in 7.5 mg/kg Nanoparticules loaded with Doxorubicin IV bolus group was important and statistically significant compared to Excipient control group (131%, p=0.003).

The increase of lung weight compared to control group was lower and not significant in 7.5 mg/kg IV perfusion group at D2 (31%, p=0.154). At D7, this increase of lung weight in perfusion group compared to control group was similar to the one observed at D2 (40%, p=0.178).

Conclusion

In the present study, we showed that a two-hour perfusion of Nanoparticules loaded with Doxorubicin at the dose level of 7.5 mg/kg did not induce delayed toxicological effects 7 days after the treatment. Indeed, most of the rats did not show lungs injury (86% of injected rats) in perfusion group 7 days after the treatment. Moreover, no difference was observed on the various observed organs two days or seven days after the treatment administration by perfusion.

Example 6

Investigation of Toxicological Effects after a Single IV Perfusion of 150 min of Nanoparticules Loaded with Doxorubicin in Healthy Wistar Rats We previously described (example 3) that a slow perfusion rate of about 120 min of Nanoparticules loaded with Doxorubicin (4.3 µL/min or 15.6 µg Doxo HCl/min) strongly reduced toxicological side effects compared to IV bolus injection at the same dose level.

The aim of the present study was to compare the impact on tolerance and lung toxicity of perfusion speed of Nanoparticules loaded with Doxorubicin suspension at the dose level of 7.5 mg/kg.

In this way, Nanoparticules loaded with Doxorubicin were administered by IV perfusion at the rates of 12.5 µg/min (corresponding to a perfusion of 150 min for a 250 g rat and for a suspension of Nanoparticules loaded with Doxorubicin at 3.7 mg/mL Doxo HCl equivalent). Rat euthanasia was performed 48 h after the treatment, according to the scheme appearance of toxicological observed effects.

Drug Administration

The study involved 41 male Wistar rats.

Rats were distributed at random to form 6 groups of 6 rats (bolus injection groups), 12 rats (Nanoparticules loaded with Doxorubicin perfusion group) and 4 rats (excipient solution perfusion) the day of the first IV treatment.

The IV injection was performed under light isoflurane anesthesia via the femoral vein in the case of a 150 min perfusion of at a rate of 12.5 µg Doxo HCl/min or 3.4 µL/min for a 250 g rat and a suspension at 3.70 mg/mL. In the case of the bolus injection via the penis vein, the injection rate was about 1000 µL/min or 3660 µg Doxo HCl/min.

To determine the real administered dose, each syringe and catheter was weighted before and after treatment.

The rats from group 1 received a single IV perfusion injection of Nanoparticules loaded with Doxorubicin (batch BA003-07C001PH) at 7.5 mg/kg equivalent Doxo HCl (Q1Dx1). Drug suspension was administered according to the body weight of rat determined just before the administration, so as to administer a dose volume of 2.02 ml/kg of a 3.70 mg/ml suspension. The perfusion rate was defined as 3.4 µL/min or 12.5 µg Doxo HCl/min for a 250 g rat (150 min perfusion).

The rats from group 2 received a single bolus IV injection of Nanoparticules loaded with Doxorubicin (batch BA003-07C001PH) at 7.5 mg/kg equivalent Doxo HCl (Q1Dx1). Drug suspension was administered according to the body weight of rat determined just before the administration, so as to administer a dose volume of 2.02 ml/kg of a 3.70 mg/ml suspension. The injection rate was defined as 1000 µL/min or 3660 µg Doxo HCl/min.

The rats from group 3 received a single IV bolus injection of Nanoparticules loaded with Doxorubicin (batch BA003-07C001PH) at 5 mg/kg equivalent Doxo HCl (Q1Dx1). Drug suspension was administered according to the body weight of rat determined just before the administration, so as to administer a dose volume of 1.34 ml/kg of a 3.70 mg/ml suspension. The injection rate was defined as 1000 µL/min or 3660 µg Doxo HCl/min.

The rats from group 4 (Nanoparticules group) received a single IV administration of the same volume of Nanoparticules that 7.5 mg/kg Nanoparticules loaded with Doxorubicin treated group. Suspension was administered according to the body weight of rat determined just before the administration, so as to administer a dose volume of 2.02 ml/kg. The injection rate was defined as 1000 µL/min.

The rats from groups 5 and 6 received a single IV administration of the same volume of Excipient solution that 7.5 mg/kg Nanoparticules loaded with Doxorubicin treated group at a bolus rate of 1000 µL/min (Excipient bolus control group) and a perfusion rate of 3.4 and 4.2 µL/min (Excipient perfusion control group). Solution was administered according to the body weight of rat determined just before the administration. Treatment allocation was performed as follow:

TABLE 11

Treatment allocation of rats at the day of administration

| Group | No of animals per group | Treatment | Route | Dose mg/kg, equivalent Dox-HCl | Quantity of equivalent Dox-HCl (mg, rat weight = 250 g) | Dose mg/kg, equivalent PIHCA |
|---|---|---|---|---|---|---|
| 1 | 12 | Nanoparticules loaded with Doxorubicin BA003-07C001PH | IV, perfusion | 7.5 | 1.875 | 99.75 |
| 2 | 6 | Nanoparticules loaded with Doxorubicin BA003-07C001PH | IV, bolus | 7.5 | 1.875 | 99.75 |
| 3 | 6 | Nanoparticules loaded with Doxorubicin BA003-07C001PH | IV, bolus | 5 | 1.250 | 66.5 |
| 4 | 6 | Nanoparticulss | IV, bolus | — | — | 99.75 |
| 5 | 6 | Excipient Control | IV, bolus | — | — | — |
| 6 | 4 | Excipient Control | IV, perfusion | — | — | — |

Mortality

Mortality was observed only in 7.5 mg/kg IV bolus treated group. Four rats were found dead 48 h after the treatment (66.7% of injected rats).

There was no difference in survival between Excipient control group, 7.5 mg/kg IV perfusion group, 5 mg/kg bolus group and Nanoparticules group.

TABLE 12

Mortality follow-up

| Treatment | Mortality at D1 | Mortality at D2 |
|---|---|---|
| Nanoparticules loaded with Doxorubicin BA003-07C001PH, 7.5 mg/kg IV bolus | 0/6 (0%) | 4/6 (66.7%) |
| Nanoparticules loaded with Doxorubicin BA003-07C001PH, 7.5 mg/kg IV perfusion | 0/12 (0%) | 0/12 (0%) |
| Nanoparticules loaded with Doxorubicin BA003-07C001PH, 5 mg/kg IV bolus | 0/6 (0%) | 0/6 (0%) |
| Nanoparticules IV bolus | 0/6 (0%) | 0/6 (0%) |
| Excipient Control IV bolus | 0/6 (0%) | 0/6 (0%) |

Macroscopic Lungs Examination

Major lung injuries were observed in 7.5 mg/kg IV bolus treated group. These physiological alterations were characterized by the presence of fluid in the thoracic cavity, the increase of lung weight and hemorrhagic lungs for dead rats. Lungs with non homogeneous colour and with black dots were observed for one surviving rat/2. We did not observe any exudates in the thoracic cavity and no macroscopic lung alterations in 7.5 mg/kg Nanoparticules loaded with Doxorubicin IV perfusion group, 5 mg/kg IV bolus treated group, Nanoparticules group and in Excipient control bolus group. It is to note that lungs could present non homogeneous colour in these groups.

No macroscopic lung alteration was observed in Excipient control perfusion groups (3.4 or 4.2 µL/min) euthanatized just after the treatment.

TABLE 13

Summary of incidence of macroscopic lung injuries

| Treatment | Number of rats | Incidence of macroscopic lung injuries |
|---|---|---|
| Nanoparticules loaded with Doxorubicin BA003-07C001PH, 7.5 mg/kg IV bolus | 6 | 5/6 |
| Nanoparticules loaded with Doxorubicin BA003-07C001PH 7.5 mg/kg IV perfusion 150 min | 12 | 0/12 |
| Nanoparticules loaded with Doxorubicin BA003-07C001PH 5 mg/kg IV bolus | 6 | 0/6 |
| Nanoparticules IV bolus | 6 | 0/6 |
| Excipient bolus control | 6 | 0/6 |
| Excipient perfusion control | 4 | 0/4 |

Lung Weight

The mean lung weight of each Nanoparticules loaded with Doxorubicin was compared to the mean lung weight of Excipient bolus control group.

The increase of lung weight in 7.5 mg/kg Nanoparticules loaded with Doxorubicin IV bolus group was important compared to Excipient bolus control group (124.2%, p=0.007). No increase of lung weight was observed in 7.5 mg/kg Nanoparticules loaded with Doxorubicin perfusion group compared to control group (2.1%, p=0.472). Moreover, the increase of lung weight in 5 mg/kg and Nanoparticules groups was minor compared to excipient bolus control group with respectively 5.4% (p=0.349) and 7.9% (p=0.051).

Conclusion

The present study showed that decreasing the perfusion speed from 15.6 μg Doxo HCl/min to 12.5 μg/min still reduced the impact of the treatment on lungs, as no mortality was observed in perfusion group and the mean lung weight was similar to control excipient group. In comparison, the mean lung weight was increased of 124% in 7.5 mg/kg bolus group.

Example 7

Clinical Study Phase III

The study primarily aims at demonstrating the efficacy of slow IV infusions of Nanoparticules loaded with Doxorubicin in patients with advanced HCC.

Trial Design

The study is a multicentre, randomized, controlled, open-label study comparing the efficacy and safety of slow repeated intravenous infusion of 2 doses of Nanoparticules loaded with Doxorubicin (20 mg/m$^2$ and 30 mg/m$^2$) to those of Best Supportive Care (BSC) in patients suffering from advanced Hepatocellular Carcinoma (HCC) after failure or intolerance to Sorafenib. The study will be carried out at multiple hepatology or oncology centres that manage patients with HCC with or without cirrhosis. Based on the survival data obtained in the phase II clinical trial, it has been calculated that 390 patients have to be included to adequately compare the efficacy of Nanoparticules loaded with Doxorubicin 20 mg/m$^2$ and Nanoparticules loaded with Doxorubicin 30 mg/m$^2$ to that of BSC. A safety evaluation will be carried out on a regular basis at least twice a year by the Data Safety Monitoring Board (DSMB) and every 25 patients or every 50 infusions of Nanoparticules loaded with Doxorubicin whichever comes first. Patients who meet the inclusion/exclusion criteria will be randomised according to a 1:1:1 ratio to receive 20 mg/m$^2$ of Nanoparticules loaded with Doxorubicin or 30 mg/m$^2$ of Nanoparticules loaded with Doxorubicin, or Best Supportive Care (BSC). Only those patients whose survival expectations is longer than 2 months and could receive more than 1 Nanoparticules loaded with Doxorubicin infusion could be included.

The study duration for each patient includes a screening period of 28 days maximum before randomization. The patient will then be randomized and either infused Nanoparticules loaded with Doxorubicin 20 mg/m$^2$ or Nanoparticules loaded with Doxorubicin 30 mg/m$^2$ over 6 hours through the IV route or given BSC. Patients will receive as many cycles as possible up to unequivocal tumor progression (assessed by the investigator), cure or occurrence of unacceptable toxicity. They will be evaluated for efficacy assessment every 2 months.

The patients randomized in Nanoparticules loaded with Doxorubicin groups will be hospitalized from Day 0 of each cycle of treatment and will be discharged on Day 3. Study treatment (20 or 30 mg/m$^2$ of Nanoparticules loaded with Doxorubicin) will be administered by infusion over 6 hours through intravenous route at Day 1 and will be repeated every 4 weeks until unequivocal progression (assessed by the investigator) or toxicity. A study visit will be performed on Day 14 of each cycle. Two months after last study drug administration, a End of Study visit will be performed.

The patients randomized in control group ("Best supportive care" group) will be receiving treatment as usual and will be followed according to the centre's usual practices. Study visits at Day 1 and Day 14 of each cycle will be mandatory.

For patient randomized in Nanoparticules loaded with Doxorubicin group, the total dose of Doxorubicin will not exceed 450 mg/m$^2$.

The Follow up survival status of all patients (including patients who prematurely withdraw) will be maintained every 3 months until death.

Subject Selection

Inclusion Criteria

All patients included in the study have to meet the following criteria for inclusion in the study:
1. Male or non-pregnant, non-breast feeding female;
2. Aged≥18 years;
3. Patient with
   advanced HCC (BCLC-C according to BCLC staging classification) having progressed (RECIST criteria) under sorafenib therapy or intolerant to sorafenib, or;
   intermediate HCC (BCLC-B) non eligible or nonresponders to transarterial chemoembolization (TACE), and having progressed under or intolerant to sorafenib therapy
4. HCC diagnosed according to the AASLD criteria:
   Cyto-histology criteria;
   Non-invasive criteria:
     Nodule≥20 mm: one imaging technique among MRI and CT scan showing arterial enhancement;
     Nodule 10-20 mm: two imaging techniques showing arterial enhancement and portal wash-out;
5. Without cirrhosis or with non decompensated cirrhosis and a Child-Pugh score from A5 to B7 included
6. ECOG Performance Status 0 or 1;
7. Laboratory tests as follows:
   Platelets≥50,000/mm3
   Neutrophil count≥1000/mm3
   Hemoglobin≥10 g/dL
   Serum transaminases<5 ULN(NCI/CTC grades 0, 1, or 2)

Alkaline phosphatases<5 ULN(NCI/CTC grades 0, 1, or 2)

Serum bilirubin<35 μM/L (or 2.0 mg/dL);

8. Signed and dated written informed consent form.

The invention claimed is:

1. A method for reducing, in a cancer patient, the occurrence or severity of macroscopic lung injuries induced by nanoparticles that comprise:
at least one chemotherapeutic antitumoral agent that is doxorubicin or a pharmaceutically acceptable salt thereof,
at least one poly(alkylcyanoacrylate), and
at least one cyclodextrin,
the method comprising administering the nanoparticles to the cancer patient by intravenous infusion for at least 2 hours;
wherein the macroscopic lung injuries induced by the nanoparticles occur two or more days after infusion;
wherein the dosage of doxorubicin or pharmaceutically acceptable salt thereof administered by said intravenous infusion is from about 10 to about 30 mg/m$^2$.

2. The method according to claim 1, wherein the nanoparticles are administered by intravenous infusion for between 2 and 24 hours.

3. The method according to claim 1, wherein the nanoparticles are administered by intravenous infusion for between 4 and 12 hours.

4. The method according to claim 1, wherein the nanoparticles are administered by intravenous infusion for about 6 hours.

5. The method according to claim 1, wherein said at least one poly(alkylcyanoacrylate) is a poly($C_6C_8$ alkylcyanoacrylate).

6. The method according to claim 1, wherein said at least one poly(alkylcyanoacrylate) is a polyisohexylcyanoacrylate.

7. The method according to claim 1, wherein:
said at least one chemotherapeutic antitumoral agent is at a concentration from 0.01 to 200 mg/g of the nanoparticles,
said at least one cyclodextrin is in an amount of from 0.1% to 70% w/w of the nanoparticles, and
said at least one poly(alkylcyanoacrylate) is in an amount of from 1% to 25% w/w of the nanoparticles.

8. The method according to claim 7, wherein said at least one chemotherapeutic antitumoral agent is at a concentration from about 1 to about 50 mg/g of the nanoparticles.

9. The method according to claim 7, wherein said at least one cyclodextrin is in an amount of from about 1% to about 30% w/w of the nanoparticles.

10. The method according to claim 7, wherein said at least one poly(alkylcyanoacrylate) is in an amount of from about 5% to about 15% w/w of the nanoparticles.

11. The method according to claim 1, wherein the dosage of doxorubicin administered by said intravenous infusion is from about 20 to about 30 mg/m$^2$.

12. The method according to claim 1, wherein the dosage of doxorubicin administered by said intravenous infusion is about 30 mg/m$^2$.

13. The method according to claim 1, wherein the cancer patient has a hepatocellular carcinoma.

14. The method according to claim 13, wherein the cancer patient has an advanced hepatocellular carcinoma after failure or intolerance to sorafenib.

15. The method according to claim 1, wherein the cancer patient has a solid tumor.

16. The method according to claim 1, wherein the cancer patient has a hematopoietic tumor.

17. The method according to claim 1, wherein the macroscopic lung injuries induced by the nanoparticles are fatal or life-threatening macroscopic lung injuries.

18. A method for reducing, in a cancer patient, the occurrence or severity of macroscopic lung injuries induced by nanoparticles that comprise:
at least one chemotherapeutic antitumoral agent that is doxorubicin or a pharmaceutically acceptable salt thereof,
at least one poly(alkylcyanoacrylate), and
at least one cyclodextrin,
the method comprising administering the nanoparticles to the cancer patient by intravenous infusion for about 6 hours;
wherein the macroscopic lung injuries induced by the nanoparticles occur two or more days after infusion;
wherein the dosage of doxorubicin or pharmaceutically acceptable salt thereof administered by said intravenous infusion is from about 20 to about 30 mg/m$^2$;
wherein the cancer patient has an advanced hepatocellular carcinoma after failure or intolerance to sorafenib.

19. A method for reducing, in a cancer patient, the mortality associated with macroscopic lung injuries induced by nanoparticles that comprise:
at least one chemotherapeutic antitumoral agent that is doxorubicin or a pharmaceutically acceptable salt thereof,
at least one poly(alkylcyanoacrylate), and
at least one cyclodextrin,
the method comprising administering the nanoparticles to the cancer patient by intravenous infusion for at least 2 hours;
wherein the macroscopic lung injuries induced by the nanoparticles occurs two or more days after infusion;
wherein the dosage of doxorubicin or pharmaceutically acceptable salt thereof administered by said intravenous infusion is from about 10 to about 30 mg/m$^2$.

20. A method for reducing, in a cancer patient, the occurrence of fatal respiratory distress induced by nanoparticles that comprise:
at least one chemotherapeutic antitumoral agent that is doxorubicin or a pharmaceutically acceptable salt thereof,
at least one poly(alkylcyanoacrylate), and
at least one cyclodextrin,
the method comprising administering the nanoparticles to the cancer patient by intravenous infusion for at least 2 hours;
wherein the fatal respiratory distress induced by the nanoparticles occurs two or more days after infusion;
wherein the dosage of doxorubicin or pharmaceutically acceptable salt thereof administered by said intravenous infusion is from about 10 to about 30 mg/m$^2$.

* * * * *